United States Patent
Imberty et al.

(10) Patent No.: US 9,023,814 B2
(45) Date of Patent: May 5, 2015

(54) GLYCOMIMETIC COMPOUNDS AS ANTI-INFECTIOUS AGAINST PATHOGENS LECTINS

(75) Inventors: Anne Imberty, Claix (FR); Sébastien Vidal, Villeurbanne (FR); Susan Matthews, Norwich (GB); Karine Faure, Lille (FR); Benoit Guery, Lille (FR); Samy Cecioni, Lyons (FR)

(73) Assignees: Centre National de la Recherche Scientifique, Paris Cedex (FR); Universite Claude Bernard—Lyon 1, Villeurbanne (FR); Universite Lille 2—Droit et Sante, Lille (FR)

( * ) Notice: Subject to any disclaimer, the term of this patent is extended or adjusted under 35 U.S.C. 154(b) by 0 days.

(21) Appl. No.: 13/992,447

(22) PCT Filed: Dec. 10, 2010

(86) PCT No.: PCT/IB2010/055741
§ 371 (c)(1), (2), (4) Date: Jun. 7, 2013

(87) PCT Pub. No.: WO2012/076934
PCT Pub. Date: Jun. 14, 2012

(65) Prior Publication Data
US 2013/0252910 A1 Sep. 26, 2013

(51) Int. Cl.
C07H 5/06 (2006.01)
C07H 15/18 (2006.01)
C07H 17/08 (2006.01)
C07H 3/06 (2006.01)
C07H 17/02 (2006.01)

(52) U.S. Cl.
CPC ............... *C07H 17/08* (2013.01); *C07H 3/06* (2013.01); *C07H 5/06* (2013.01); *C07H 17/02* (2013.01)

(58) Field of Classification Search
CPC .................................. C07H 5/06; C07H 15/18
See application file for complete search history.

(56) References Cited

PUBLICATIONS

Cecioni et al., Chemistry—A European Journal, vol. 15 (47), 2009, pp. 13232-13240.*
International Search Report for PCT/IB2010/055741, mailed Apr. 11, 2011, (Nikolai, Joachim).

(Continued)

*Primary Examiner* — Traviss C McIntosh, III
(74) *Attorney, Agent, or Firm* — Nixon & Vanderhye P.C.

(57) ABSTRACT

The present invention relates to a calixarene-based glycosylated compound (I) having the formula: (I) wherein D is independently selected in the group comprising a —CH$_2$- group, an oxygen atom, a sulphur atom, a sulfinyl group or a sulfonyl group, E is independently selected in the group comprising a hydrogen, an alkyl having from 1 to 10 carbon atoms, an aryl having from 6 to 20 carbon atoms, a nitrogen dioxide group, an azide group, an amino group, a guanidinium group, a halogen atom, a —CH$_2$ R group wherein R is a hydroxyl, a halogen, an amino group, a N(alkyl)$_2$ group, a NH(alkyl) group, or E represents a —CO—R' wherein R' is a hydrogen atom, a hydroxyl group or an amino, B represents a A-C group wherein A is independently selected in the group comprising an oxygen atom, a sulfur atom, a NH group or a (CH$_2$)$_i$ group, i being an integer from 1 to 10, C is independently selected in the group comprising a hydrogen, an alkyl, an alkenyl, an alkynyl, or C is a group of formula (II). The present invention also relates to a pharmaceutical composition characterized in that it comprises the said calixarene-based glycosylated compound (I), in combination with pharmaceutically acceptable carriers or diluents. The present invention also relates to the use of the said calixarene-based glycosylated compound (I) or the said pharmaceutical composition, for the manufacture of a drug intended to prevent or treat bacterial infections from pathogens that use lectins in the first steps of infection.

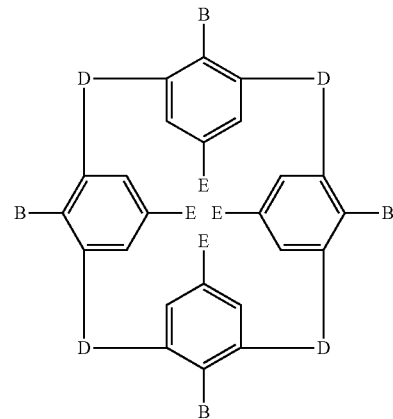

(I)

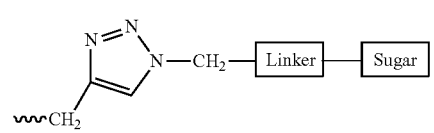

(II)

10 Claims, 7 Drawing Sheets

(56) References Cited

PUBLICATIONS

Figure 1A:
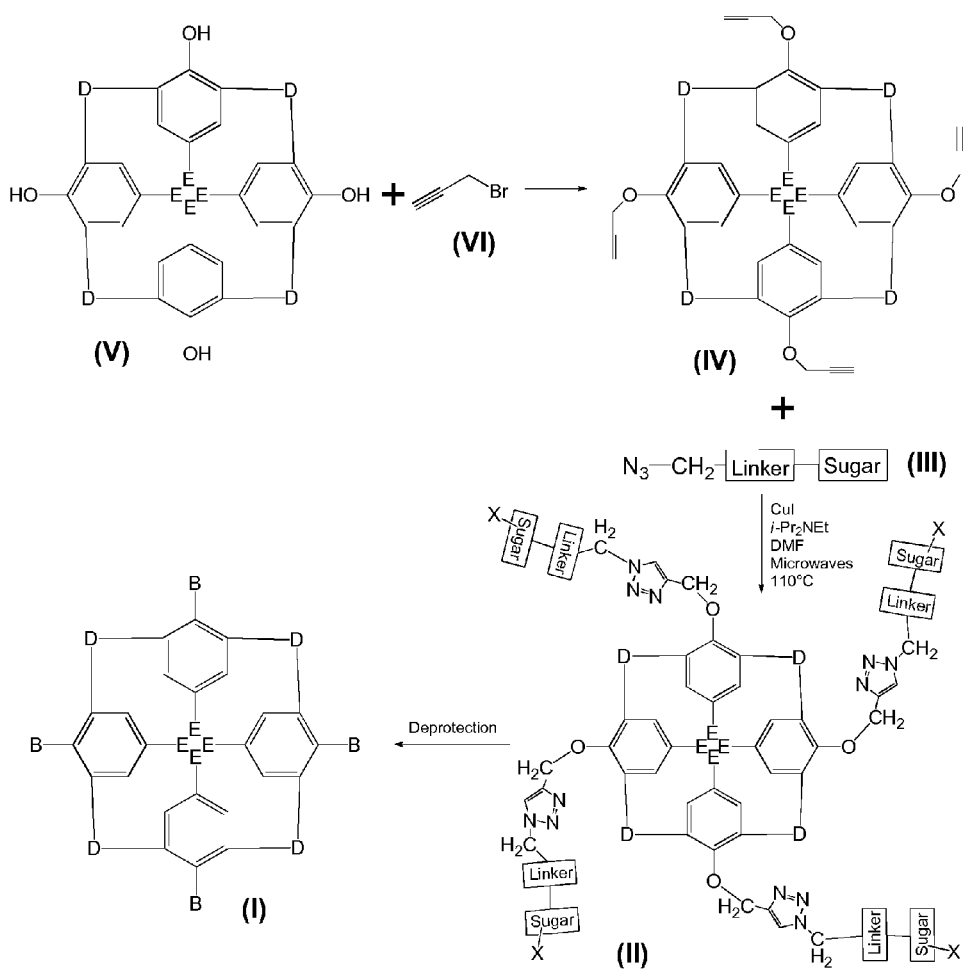

Cecioni, Samy et al., "Achieving High Affinity towards a Bacterial Lectin through Multivalent Topological Isomers of Calix[4]arene Glycoconjugates", Chemistry—A European Journal, 15(47), (2009).
Marra, Alberto et al., "Synthesis of sialoclusters appended to calyx[4]arene platforms via multiple azide-alkyne cycloaddition. New inhibitors of hemagglutination and cyutopathic effect mediated by BK and influenza A viruses", Organic & Biomolecular Chemistry, 6(8), (2008).

* cited by examiner

(3b-1)

(3b-2)

(3b-3)

(3c-1)

(3c-2)

(3c-3)

GLYCOMIMETIC COMPOUNDS AS ANTI-INFECTIOUS AGAINST PATHOGENS LECTINS

This application is the U.S. national phase of International Application No. PCT/IB2010/055741, filed 10 Dec. 2010, which designated the U.S., the entire contents of which is hereby incorporated by reference.

The present invention relates to glycomimetic compounds as anti-infectious against pathogens that use lectins in the first steps of infection.

*Pseudomonas aeruginosa*, also called the pyocyanic *bacillus*, is a gram negative bacterium that lives in humid environment and soil. It is associated with human activities and is present in kitchen, bathroom, hospitals etc. This opportunistic bacterium is responsible of severe nosocomial infections in immunocompromised patients, a population that is increasing with the larger number of transplantations. In France, *P. aeruginosa* has been responsible of 8% of nosocomial infections during the period from August 2001 to June 2006 (Institut de veille sanitaire, BHE 30-31, 2008). It is a common cause of infection of burns, but also eyes and ears, and it is also responsible of the majority of colonisation on medical devices such as catheters.

*P. aeruginosa* bacterium is also a major causative agent of lung infections in cystic fibrosis (CF) patients. In most cases, CF patients suffer from chronic pulmonary infection when they reach teenager development. These infections are the major cause of morbidity and mortality. Once chronic infection is established, it is very difficult or even impossible to eradicate it because of the occurrence of many strains that present multi-resistance to antibiotics. The formation of *P. aeruginosa* biofilms that results in increasing resistance to host immunity and to antibiotics also complicates the therapeutical approach. The rapid emergence of many pathogenic microorganisms presenting resistance towards drug compounds such as antiviral or antibiotics is a major concern for public health. The need for alternative therapeutical strategies is now urgent.

*P. aeruginosa* produces a large number of protein receptors that are able to specifically recognize carbohydrates. These receptors, called lectins, play a role in adhesion to host tissue and in biofilm formation. The lectins are either produced in soluble form in the bacteria or present at the apex of adhesives organelles. LecA (PA-IL) and LecB (PA-IIL) are soluble lectins that are produced in the cytoplasm of *P. aeruginosa* but have also been detected in large quantity on the outer membrane of the bacterial cells. LecA and LecB are both tetrameric protein and recognize galactose and fucose, respectively, in a calcium-dependant way (Gilboa-Garber, Methods Enzymol. 1982, 83, 378-385). They are considered as virulence factors for the bacteria and are co-expressed with enzymes and other proteins during infection. LecA has been demonstrated to be toxic to airway cells (Bajolet-Laudinat et al. Infect. Immun. 1994, 62, 4481-4487) and also plays a role in the formation and stabilisation of the bacteria biofilm. LecB is also involved in biofilm formation (Tielker et al., Microbiology 2005, 151, 1313-1323) and inhibits ciliary beating in lung cells in culture (Adam et al., Am. J. Respir. Crit. Care Med. 1997, 155, 2102-2104).

In many cases, the infectious process is initiated by the specific recognition of host epithelia glycoconjugates by bacterial receptors referred to as lectins. The carbohydrate specificity of these lectins determines the targeting for hosts and tissues. The recognition step is followed by adhesion, a process that triggers many cellular pathways in both the bacteria and host therefore influencing the next step of invasion and colonisation. Blocking the adhesion by glycocompounds that act as soluble analogs of glycoconjugates (here called "glycomimetics" in opposition with the natural sugars or glycoconjugates) is therefore one possible strategy against infection. Such glycomimetics enter in competition with the natural glycoconjugates present on the human tissues and thus block the bacteria adhesion and the development of colonies. Characterizing the interaction between bacterial lectins and host glycoconjugates has been a necessary step for the design of glycomimetics that can interfere in the process, and therefore limit the bacterial adhesion and/or the formation of biofilms.

Carbohydrates and derivatives are a promising source of anti-infectious compounds since many infections are initiated by the adhesion of the microorganisms on the host cell surface. Rather than killing the bacteria by antibiotics, a process that induces emergence of resistant strains, the proposed alternative is to interfere with the adhesion process. The characterisation of the natural oligosaccharides involved in the bacterial adhesion helps in the design of soluble analogues (ie the glycomimetics) that are able to compete with the cell surface glycoconjugates. The advantages of antibacterial glycomimetics are their local use and their absence of toxicity. Furthermore, the risk of resistance is weak since it does not affect directly the bacteria metabolism. Finally, such compounds can be used in conjunction with other treatments, such as antibiotics.

The glycomimetic compounds are thus a route of interest for inhibiting the adhesion of pathogens to human tissues and some of them have already been developed for bacterial infection affecting gastro-intestinal track, urinary track or ears. Recently, glycomimetics designed against FimH, a lectin present on pili of uropathogenic *E. coli*, were demonstrated not only to block adhesion of bacteria on bladder epithelia but also to inhibit biofilm production (Wellens et al., PLoS One. 2008, 3, 2040).

WO 2005/089733, WO 2007/021721 and WO 2007/143052 documents disclose oligosaccharides targeted to some bacterial infections.

However, when developing glycomimetics, one has to remember that a strong affinity is required in order to get efficient competition with cell surface glycoconjugates, and it is not always easy to develop such glycomimetics. Lectin-carbohydrate interactions are often characterized by low affinity (millimolar range) and this has been a major barrier in the development of biologically active glycomimetic compounds. It has been demonstrated that multivalency is an efficient strategy for significantly increasing the interaction between the compounds and the target. Several approaches have been used, ranging from low valency for the glycoclusters to high valency for the glycodendrimers or glycopolymers. Glycodendrimers directed against FimH demonstrated to be efficient as anti-adhesive compounds against uropathogenic *E. coli* (Touaibia et al., Chem Med Chem. 2007, 2, 1190-1201). Recently fucose-presenting glycodendrimers were used for dispersing biofilms from several strains of *P. aeruginosa* (Johansson et al., Chem Biol 2008, 15, 1249-1257). These results confirm the potential of glycomimetic for fighting bacterial infections and demonstrate that they can be used in anti-adhesion strategies.

Recently, the Inventors of the present invention have published (Cecioni et al. Chem. Eur. J. 2009, 15, 13232-13240) glycomimetics compounds which are calixarene glycoconjugates and which were evaluated as ligands for the galactose-binding lectin PA-IL from the opportunistic bacterium *P. aeruginosa*. The results show that a calixarene glycoconjugate bearing four sugars is the strongest inhibitor for binding of PA-IL to galactosylated surfaces for potential applications as an anti-adhesive agent.

The interesting results obtained in this work have encouraged the Inventors to pursue their search in order to find some novel compounds presenting anti-adhesive properties and having high affinity towards bacterial lectins.

However finding such compounds is not easy. The affinity of the glycomimetics for the lectins, and therefore its efficiency, does not depend only on the number of sugars displayed by the calixarene glycoconjugates, i.e. the valency, but also on the length and flexibility of the linkers of the calixarene glycoconjugates, said linkers connecting the sugar moiety to the calixarene moiety.

Based on the calixarene moiety that provides valency varying from 1 to 4, it is therefore necessary to develop new classes of molecules, based on new linkers bringing different properties to the final glycomimetics compounds.

Therefore there is still need for new development to obtain novel glycomimetic compounds having high affinity against pathogen lectins and anti-infectious activity.

One aim of the present invention is to provide novel glycomimetic compounds able to selectively block the lectin A and/or the lectin B from *Pseudomonas aeruginosa*.

Another aim of the present invention is to provide novel glycomimetic compounds able to limit the pathogens adhesion and therefore with strong antimicrobial activity.

Another aim of the present invention is to provide novel glycomimetic compounds able to inhibit biofilm formation and therefore of interest as anti-infectious compound against mucoid bacteria In an aspect, the present invention provides a calixarene-based glycosylated compound (I) having the formula:

(I)

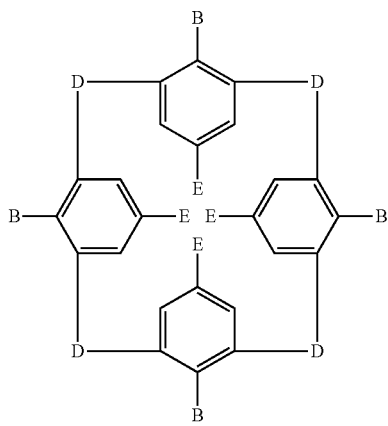

wherein
D is independently selected in the group comprising a —CH$_2$— group, an oxygen atom (—O—), a sulphur atom (—S—), a sulfinyl group

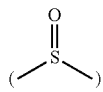

or a sulfonyl group

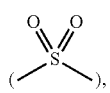

E is independently selected in the group comprising a hydrogen (H), an alkyl having from 1 to 10 carbon atoms, an aryl having from 6 to 20 carbon atoms, a nitrogen dioxide group

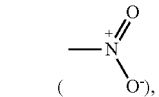

an azide group (—N=N$^+$=N$^-$), an amino group (—NH$_2$), a guanidinium group

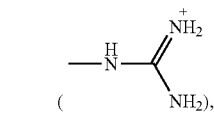

a halogen atom, a —CH$_2$R group wherein R is a hydroxyl (OH), a halogen, an amino group, a N(alkyl)$_2$ group, a NH(alkyl) group, or E represents a CO—R'

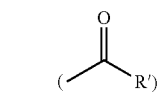

wherein R' is a hydrogen atom, a hydroxyl group or an amino,

B represents a AC group wherein

A is independently selected in the group comprising an oxygen atom, a sulfur atom, a NH group or a (CH$_2$)$_i$ group, i being an integer from 1 to 10, C is independently selected in the group comprising a hydrogen, an alkyl, an alkenyl, an alkynyl, or C is a group of formula:

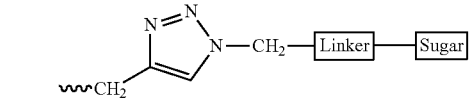

wherein the linker is a group of formula:

(CO—NH)$_n$—(V)$_m$—U wherein n is an integer from 1 to 3,

V=CH$_2$, C$_6$H$_4$ (phenyl "Ph"), CH$_2$CH$_2$—O—CH$_2$, CH$_2$CO—NH—CH$_2$, m is an integer from 1 to 15, U is absent or is CH$_2$, the sugar is a group having at least one carbohydrate moiety and is selecting in the group comprising:

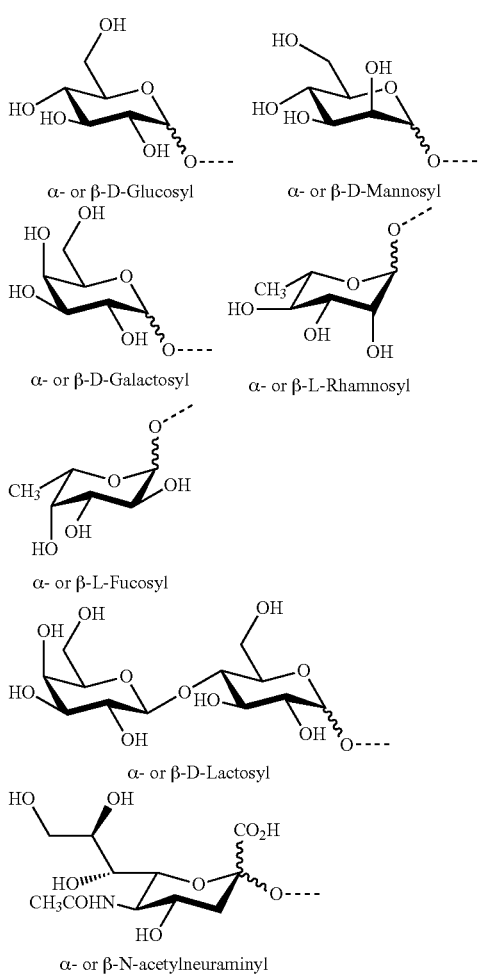

α- or β-D-Glucosyl
α- or β-D-Mannosyl
α- or β-D-Galactosyl
α- or β-L-Rhamnosyl
α- or β-L-Fucosyl
α- or β-D-Lactosyl
α- or β-N-acetylneuraminyl or their derivatives, and wherein at least one of the four C groups of the calixarene-based glycosylated compound (I) represents the group of formula:

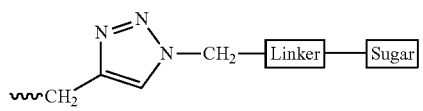

as defined above.

The calixarene-based glycosylated compound (I) as defined in the present application could also be defined as a glycomimetic compound comprising a core having at least one arm and at most four arms, the arm being represented by the following C group

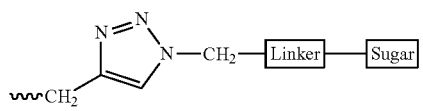

and the core being defined as the remainder of the formula (I).

The term "glycomimetic compound" as used in the present application refers more particularly to a compound (including physiologically acceptable salts thereof) that has high affinity for the Lec A, Lec B or both lectins from *Pseudomonas aeruginosa* bacteria.

The originality of the present invention lies in the particularly structure of the linker which is constituted in two parts.

The first part of the linker (located next the triazole moiety

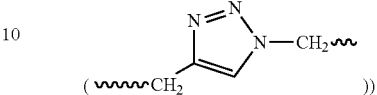

is an amide bond —(CONH)—; this planar amide bond provides some rigidity to the first part of the linker and allows for optimal presentation of the arms (number varying from 1 to 4) towards the lectin binding site.

The second part of the linker (located next the carbohydrate moiety) is variable and is represented by the structure $(V)_m$—U as defined above. This second variable part of the linker can represents a group comprising also an amide bond, an ethyleneglycol moiety or an aromatic moiety. These variable second parts will have different flexibilities and can therefore display different affinities towards lectins.

The interactions of the newly designed glycomimetics with LecA were shown to display higher affinities in comparison with the non-amide functionalized compounds previously reported (Cecioni et al., 2009). Since the affinities measured are improved for such newly designed glycomimetics, the anti-adhesive properties of such molecules can therefore be really envisioned.

The term "alkyl" used herein refers to a monoradical branched or unbranched saturated hydrocarbon chain having from 1 to 10 carbon atoms. This term is exemplified by groups such as methyl, ethyl, n-propyl, iso-propyl, n-butyl, sec-butyl, iso-butyl, tert-butyl, n-hexyl, n-octyl, tert-octyl, n-decyl and the like.

The term "aryl" refers to an unsaturated aromatic carboxylic group of from 6 to 20 carbon atoms, having a single ring or multiple condensed (fused) ring. This term is exemplified by groups such as phenyl, naphthyl and the like.

The halogen atom is exemplified by a fluorine (F), a chlorine (Cl), a bromine (Br) or an iodine (I).

The term "alkenyl" used herein refers to a monoradical of a branched or unbranched unsaturated hydrocarbon group preferably having from 2 to 10 carbon atoms and having from 1 to 6 sites of vinyl unsaturation. This term is exemplified by groups such as ethenyl (—CH=CH$_2$), n-propenyl (—CH$_2$—CH=CH$_2$), iso-propenyl (—C(CH$_3$)=CH$_2$) and the like.

The term "alkynyl" refers to a monoradical of an unsaturated hydrocarbon preferably having from 2 to 10 carbon atoms and having at least from 1 to 2 sites of acetylene (triple bond) unsaturation. This term is exemplified by groups such as ethynyl (—C≡CH), propargyl (—CH$_2$—C≡CH) and the like.

When one of the four C groups of the calixarene-based glycosylated compound (I) represents the above mentioned following group:

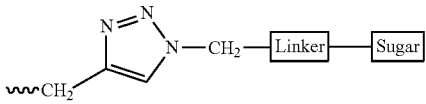

then the said calixarene-based glycosylated compound (I) can also be named "monovalent" calixarene-based glycosylated compound (I).

When two of the four C groups represent such a group, the calixarene-based glycosylated compound (I) is named "divalent".

When three of the four C groups represent such a group, the calixarene-based glycosylated compound (I) is named "trivalent".

When the four C groups represent such a group, the calixarene-based glycosylated compound (I) is named "tetravalent".

Advantageously, the above mentioned sugar derivatives in the C group are selected in the group comprising:

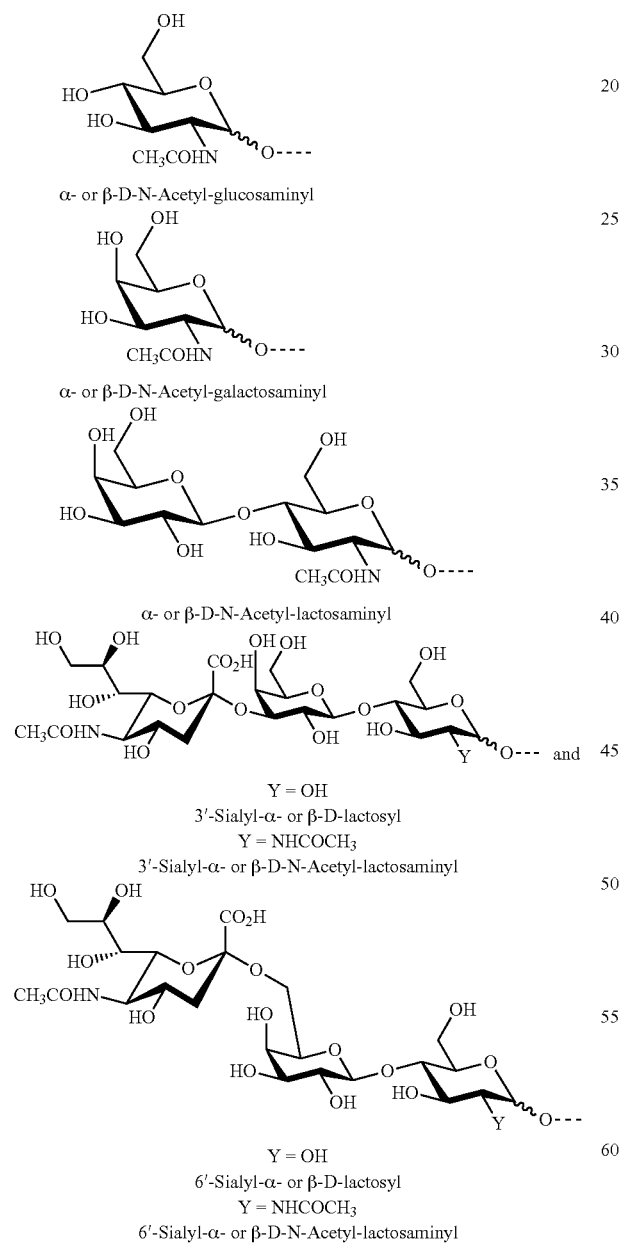

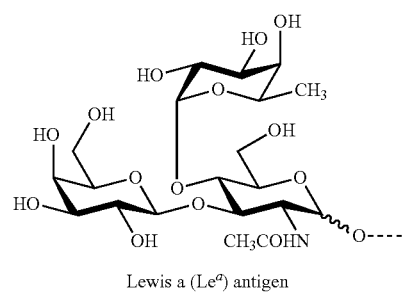

Lewis a (Le$^a$) antigen

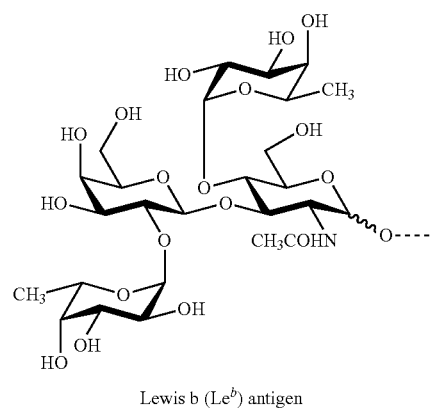

Lewis b (Le$^b$) antigen

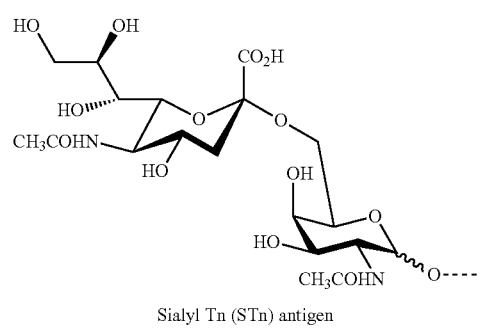

Sialyl Tn (STn) antigen

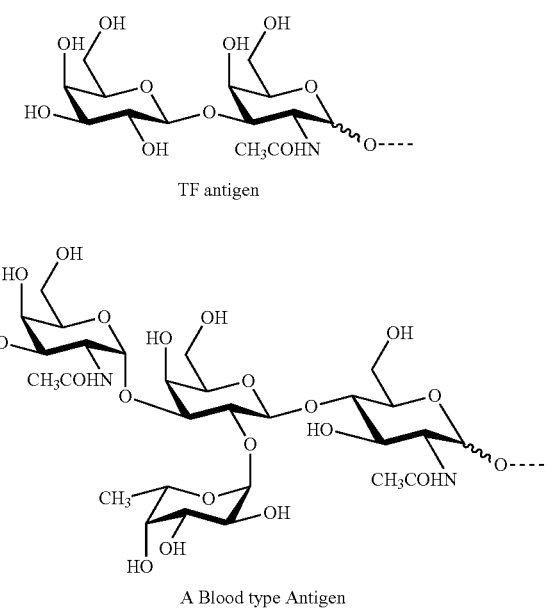

TF antigen

A Blood type Antigen

In another aspect, the above mentioned sugar derivatives in the C group are selected in the group comprising:

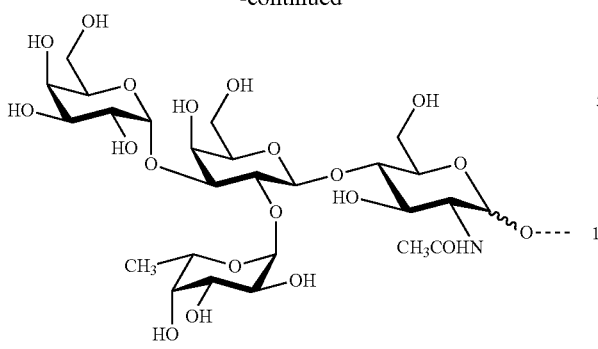

B Blood type Antigen

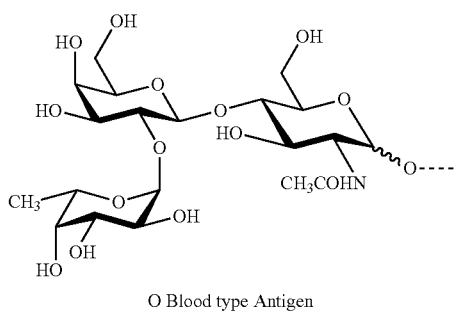

O Blood type Antigen

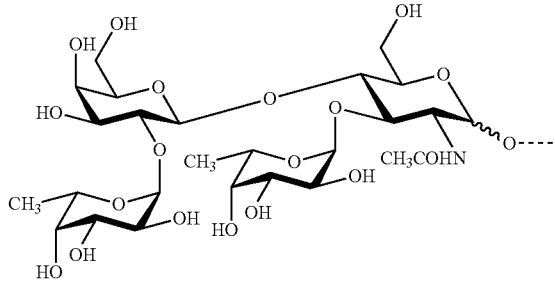

Lewis y (Le^y) antogen

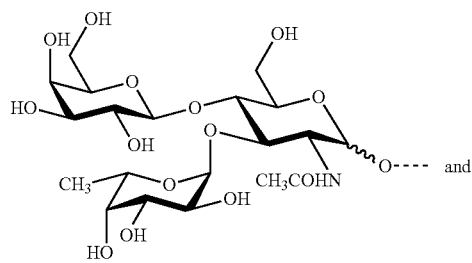

Lewis x (Le^x) antogen

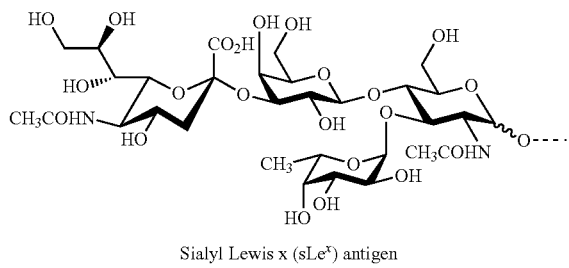

Sialyl Lewis x (sLe^x) antigen

In yet another aspect, the sugar defined in the C group of the calixarene-based glycosylated compound (I) is selected wherein the sugar defined in the C group is selected in the group comprising β-D-galactosyl, α-D-mannosyl and α-L-fucosyl. Advantageously, the sugar is the β-D-galactosyl.

Advantageously, the linker defined in the C group of the calixarene-based glycosylated compound (I) is selected in the group comprising:

n=1, m=1, V=CH$_2$CH$_2$—O—CH$_2$, U=CH$_2$, which corresponds to the following linker: CO—NH—CH$_2$CH$_2$—O—CH$_2$—CH$_2$;

n=1, m=1, V=C$_6$H$_4$ ("Ph"), U=absent, which corresponds to the following linker: CO—NH—C$_6$H$_4$;

n=1, m=1, V=CH$_2$—CO—NH—CH$_2$, U=CH$_2$, which corresponds to the following linker: CO—NH—CH$_2$—CO—NH—CH$_2$—CH$_2$.

Advantageously, the present invention provides a calixarene-based glycosylated compound (I) as defined previously, wherein two of the four C groups of the calixarene-based glycocosylated compound (I) represent the group of formula:

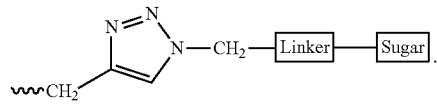

The divalent calixarene-based glycosylated compound (I) thus above defined can be represented by one of the following substitution pattern:

the 1,2-disubstituted:

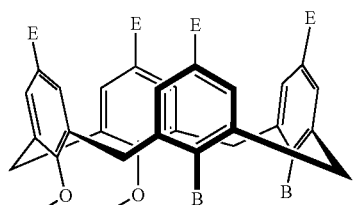

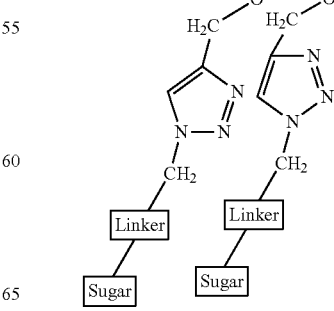

the 1,3-disubstituted:

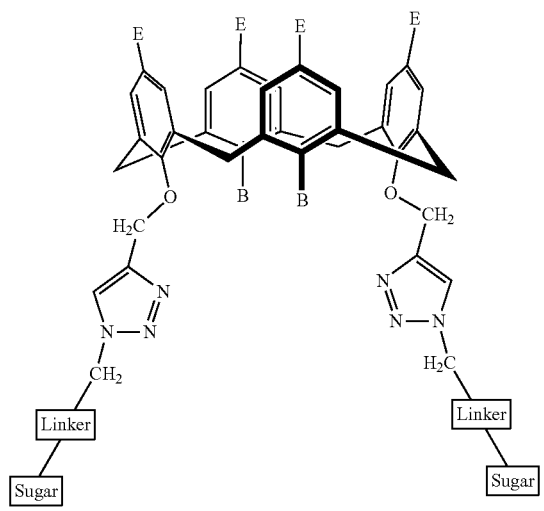

In another aspect, the present invention provides a calixarene-based glycosylated compound (I) as defined previously, wherein three of the four C groups of the calixarene-based glycosylated compound (I) represent the group of formula:

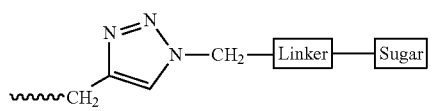

The trivalent calixarene-based glycosylated compound (I) thus above defined can be represented by the following trisubstituted conformation:

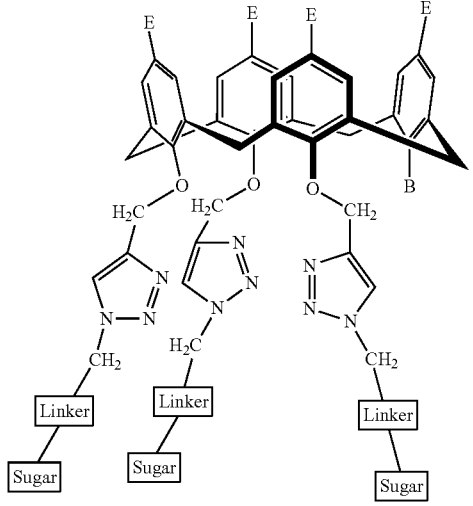

In yet another aspect, the present invention provides a calixarene-based glycosylated compound (I) as defined previously, wherein the four C groups of the calixarene-based glycosylated compound (I) represent the group of formula:

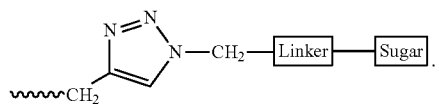

The tetravalent calixarene-based glycosylated compound (I) thus above defined can be represented by one of the four following conformations:

the cone conformation:

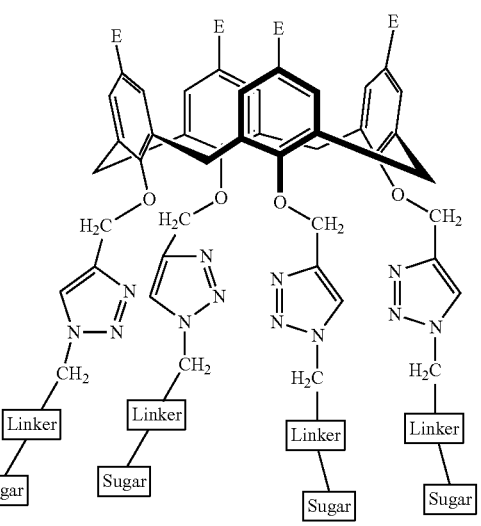

the partial cone conformation:

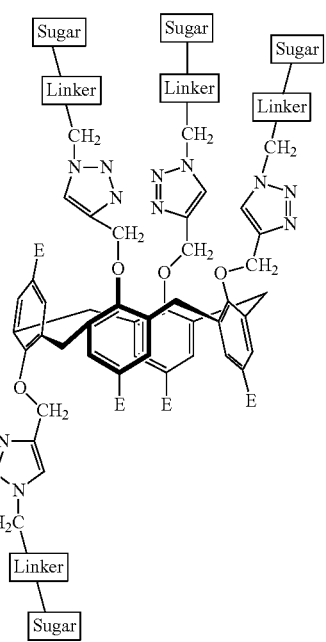

the 1,3-alternate conformation:

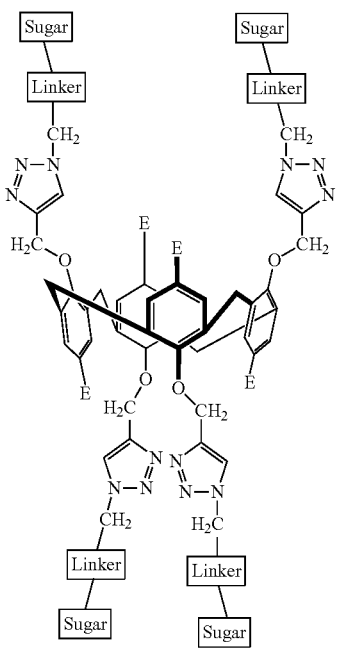

the 1,2-alternate conformation:

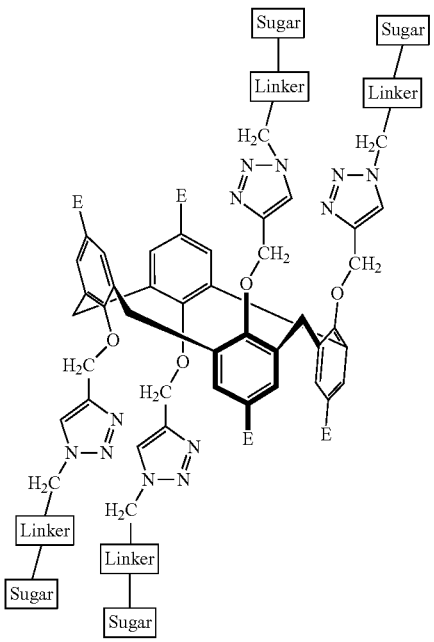

Advantageously, the present invention provides calixarene-based glycosylated compound (I) as defined previously wherein D represents a —$CH_2$— group, E represents an alkyl group which is the tert-butyl group and A defined in the B group of the calixarene-based glycosylated compound (I) represents an oxygen atom.

Another advantage of the calixarene-based glycosylated compound (I) according to invention lies to the fact that they can be obtained rapidly, according to adjustable and variable synthetics methodologies.

According to still another aspect, the invention also provides a process for the preparation of a calixarene-based glycosylated compound (I) as defined above, characterized in that it comprises the following steps:

(a) Preparation of a propargylated calix[4]arene of formula (IV):

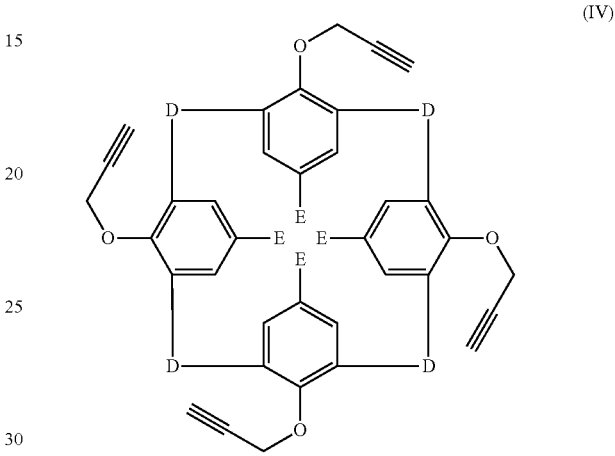

wherein D and E are as defined in claim 1,
by regioselective multi-propargylation of a calix[4]arene of formula (V):

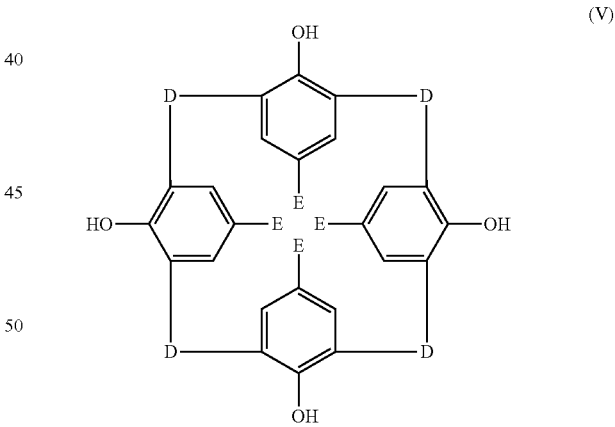

with a propargylated compound of formula (VI):

in the presence of a base to obtain the said propargylated calix[4]arene (IV), (b) Preparation of a protected calixarene-based glycosylated compound of formula (II):

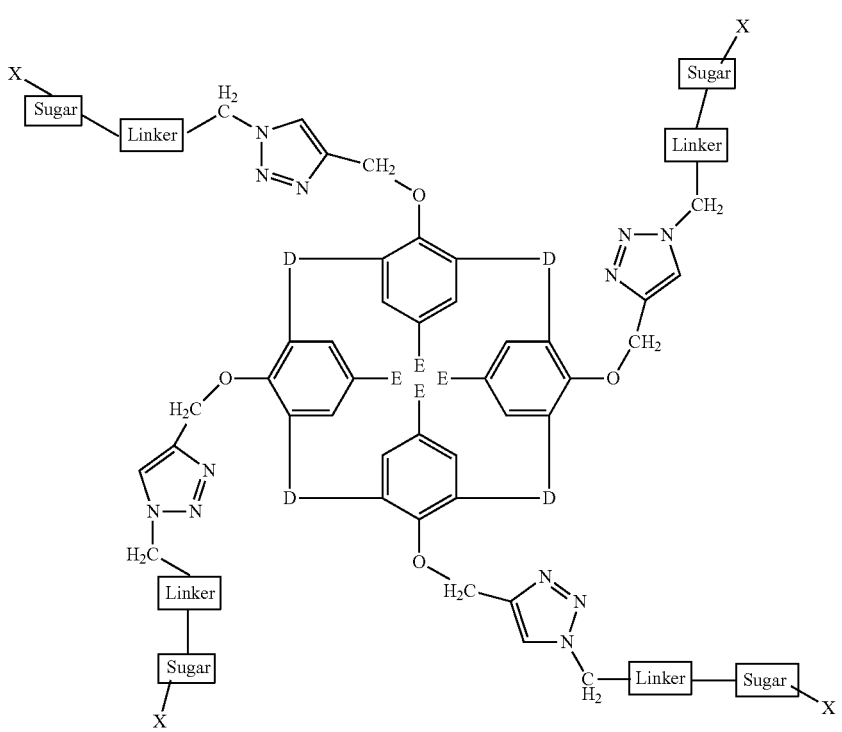

(II)

wherein
the linker and the sugar are as defined in anyone of claims 1 to 5,
X represents a protecting group selected in the group comprising acetate ($CH_3CO$), benzoate ($C_6H_5CO$) or benzyl ($C_6H_5CH_2$), this protecting group being attached to the oxygen atom of the sugar hydroxyl groups (see the formula of the sugar as represented previously),
by conjugation of the propargylated calix[4]arene (IV) as obtained in the previous step with a carbohydrate derivative of formula (III) bearing an azido functionality next to the end of the linker:

 (III)

the said carbohydrate being prepared by glycosylation with a linker bearing an alcohol function at one end and an azido group at the other end.
  (c) Obtention of the calixarene-based glycosylated compound (I) as defined in anyone of claims 1 to 10, by deprotection of the protecting groups of the said protected calixarene-based glycosylated compound of formula (II).

The base which can be used with compounds (V) and (VI) can be NaH in DMF (cone conformation) or $K_2CO_3$ then $Cs_2CO_3$. Then a mixture of partial cone and 1,3-alternate conformations is obtained which can be separated by silica gel column chromatography leading to the said propargylated calix[4]arene (IV).

The present invention also provides a pharmaceutical composition characterized in that it comprises a calixarene-based glycosylated compound (I) as defined previously, in combination with pharmaceutically acceptable carriers or diluents.

In yet a further aspect of the invention, the pharmaceutical composition thus defined also comprises a therapeutic agent useful as anti-infectious against pathogens that use lectins in the first steps of infection.

This therapeutic agent is for example a therapeutic agent for *P. aeruginosa* infection such as lung infections in cystic fibrosis patients, burns infection in hospital environment and bedsore infection in elderly houses.

The present invention also provides a calixarene-based glycoconjugate compound (I) or a pharmaceutical composition as defined previously for use as anti-infectious directed against other pathogens using lectins for adhesion to host cells, such as influenza virus.

In a further aspect, the present invention concerns the use of a calixarene-based glycoconjugate compound (I) or a pharmaceutical composition as defined previously, for the manufacture of a drug intended to prevent or treat bacterial infections from pathogens that use lectins in the first steps of infection.

Such a drug acts as anti-infectious directed against lectins from pathogens.

In another aspect of the invention, the above mentioned calixarene-based glycosylated compounds (I), pharmaceutical compositions or drugs comprising these compounds, are used by the respiratory or pulmonary way.

These compounds, drugs or compositions are inhaled or instilled in the respiratory tract for preventing or treating infections from *Pseudomonas aeruginosa*, in particular in CF patients or patients being under respiratory assistance and which are often victims of nosocomial infections.

In a further aspect of the invention, the above mentioned calixarene-based glycosylated compounds (I), pharmaceutical compositions or drugs comprising these compounds, are used by the local way or on a bandage for preventing or treating infections from *Pseudomonas aeruginosa*, in particular for burns or scabs.

The novel features of the present invention will become apparent to those of skill in the art upon examination of the following detailed description of the invention. It should be understood, however, that the detailed description of the invention and the specific examples presented, while indicating certain embodiments of the present invention, are provided for illustration purposes only because various changes and modifications within the spirit and scope of the invention will become apparent to those of skill in the art from the detailed description of the invention.

Reference is now made to the following examples in conjunction with the accompanying drawings 1 to 7.

FIG. 1a is a general synthesis scheme illustrating the chemical structures and the preparation of the tetravalent calixarene-based glycosylated compound (I) wherein the four C represent the group of formula:

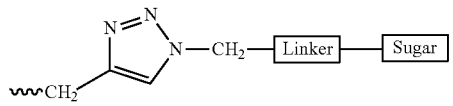

Figure 1B:
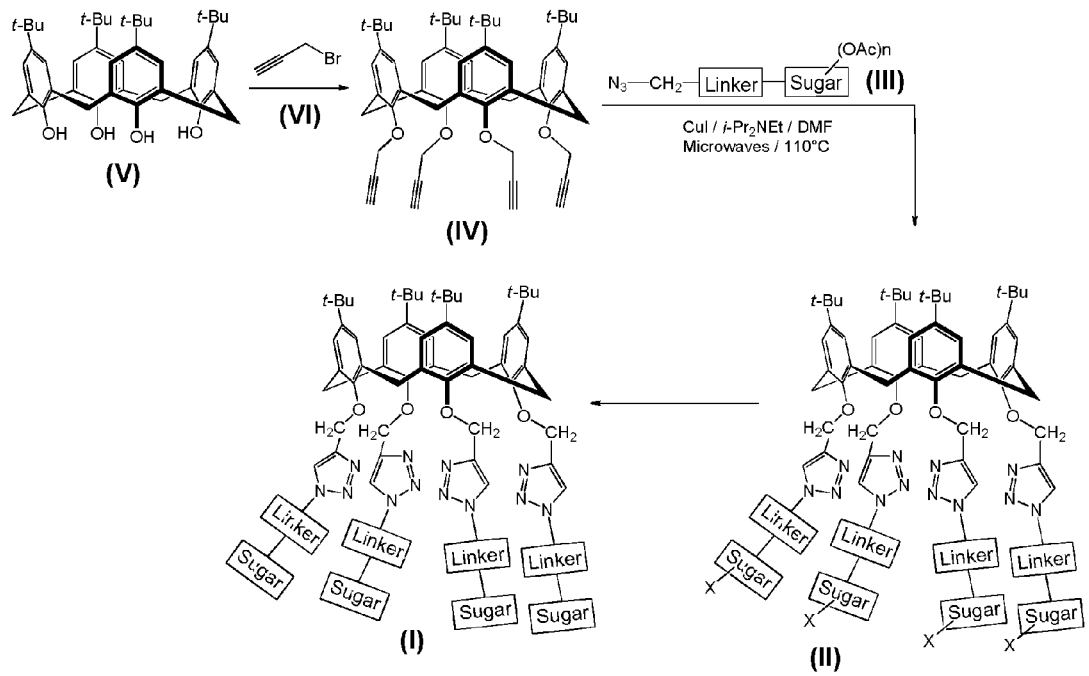

FIG. 1b is a particular example of the general synthesis scheme of FIG. 1a, wherein in the tetravalent calixarene-based glycosylated compound (I) D represents a —$CH_2$— group, E represents an alkyl group which is the tert-butyl group (t-Bu), A defined in the B group represents an oxygen atom, the linker, the sugar and X are as defined previously.

In FIGS. 1a and 1b the calixarene-based glycosylated compound (I) obtained is tetravalent. The monovalent, divalent or trivalent calixarene-based glycosylated compound (I) are however obtained in the same way as the tetravalent. The selective alkylation of the phenolic groups is achieved with a base in the presence of alkyl halides and the remaining phenolic groups are then propargylated under the same conditions as for the transformation of (V) in (IV).

Figure 2A:
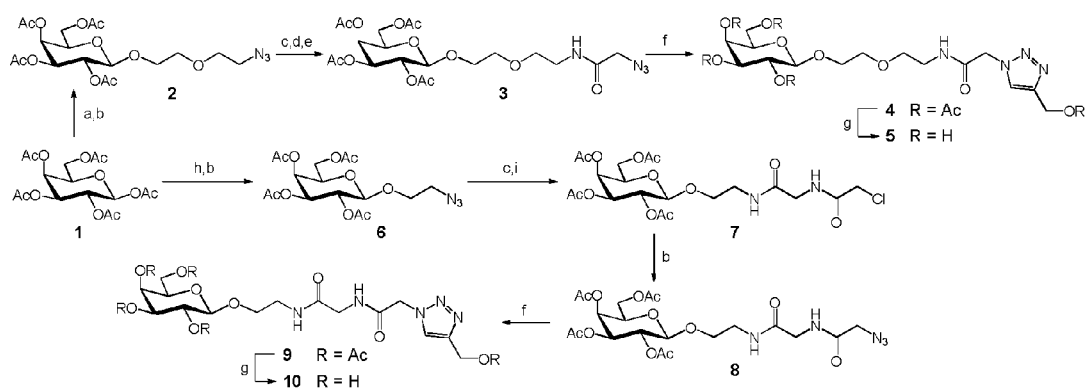

FIG. 2a represents synthesis schemes of carbohydrate azido-derivatives (III) named respectively "3" (wherein linker =CO—NH—$CH_2$—$CH_2$—O—$CH_2$—$CH_2$) and "8" (wherein linker =CO—NH—$CH_2$—CO—NH—$CH_2$—$CH_2$). The reagents and conditions of the different steps are described below. Step a): HOCH$_2$CH$_2$OCH$_2$CH$_2$Cl, SnCl$_4$, CF$_3$CO$_2$Ag, CH$_2$Cl$_2$, rt, 2 h; Step b): NaN$_3$, nBu$_4$NI, DMF, 85° C., 16 h; Step c): H$_2$, Pd—C 10%, CH$_2$Cl$_2$, rt, 16 h; Step d): BrCH$_2$COBr, Et$_3$N, CH$_2$Cl$_2$, rt, 12 h; Step e): NaN$_3$, nBu$_4$NI, DMF, 85° C., 16 h; Step f): propargyl acetate, CuI, iPr$_2$NEt, DMF, 110° C., microwaves, 15 min.; Step g): MeOH, H$_2$O, Et$_3$N, rt, 16 h; Step h): HOCH$_2$CH$_2$Cl, SnCl$_4$, CF$_3$CO$_2$Ag, CH$_2$Cl$_2$, rt, 2 h; Step i): N-chloroacetyl-glycine, EDCl, HOBt, CH$_2$Cl$_2$/DMF, rt, 16 h.

Figure 2B:
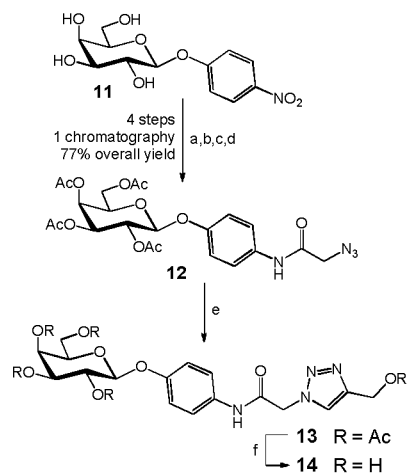

FIG. 2b represents synthesis scheme of the carbohydrate azido-derivative (III) named "12" (wherein linker =CO—NH—C$_6$H$_4$). The reagents and conditions of the different steps are described below. Step a): Ac$_2$O, C$_5$H$_5$N, DMAP, rt, 16 h; Step b): H$_2$, Pd—C 10%, CH$_2$Cl$_2$, rt, 16 h; Step c): BrCH$_2$COBr, Et$_3$N, CH$_2$Cl$_2$, rt, 2 h; Step d): NaN$_3$, nBu$_4$NI, DMF, 50° C., 16 h; Step e) propargyl acetate, CuI, iPr$_2$NEt, DMF, 110° C., microwaves, 15 min; Step f) MeOH, H$_2$O, Et$_3$N, rt, 16 h.

Figure 3A:
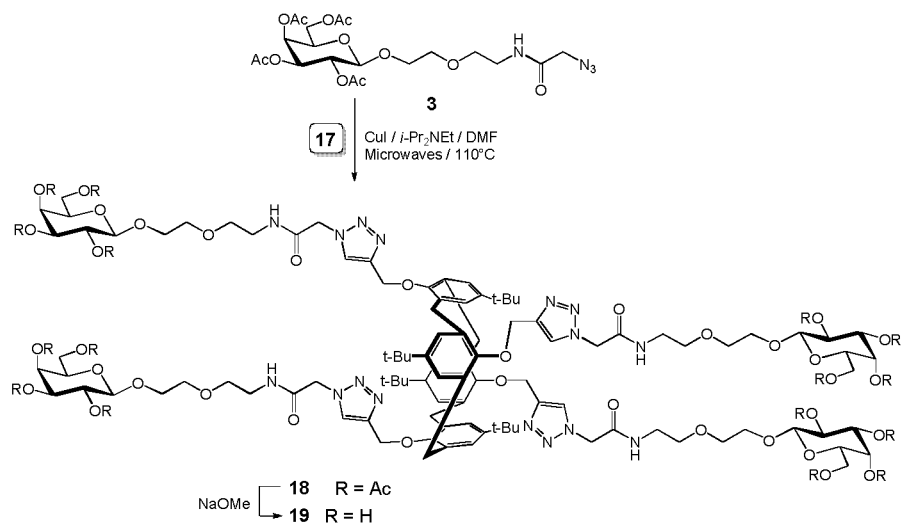
Figure 3B:
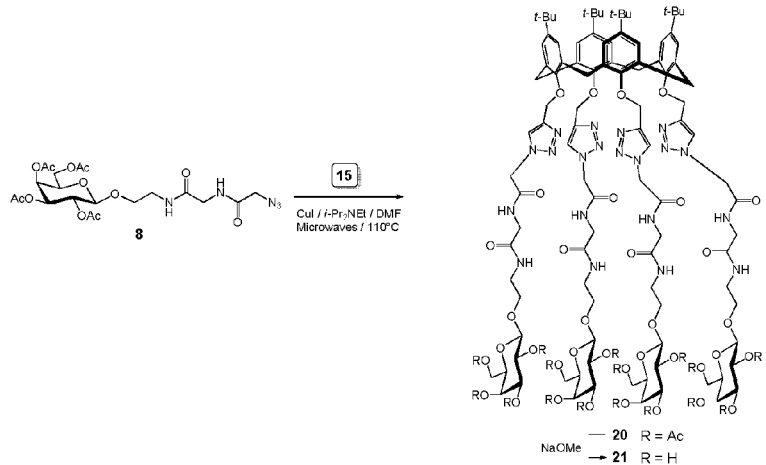
Figure 3B:
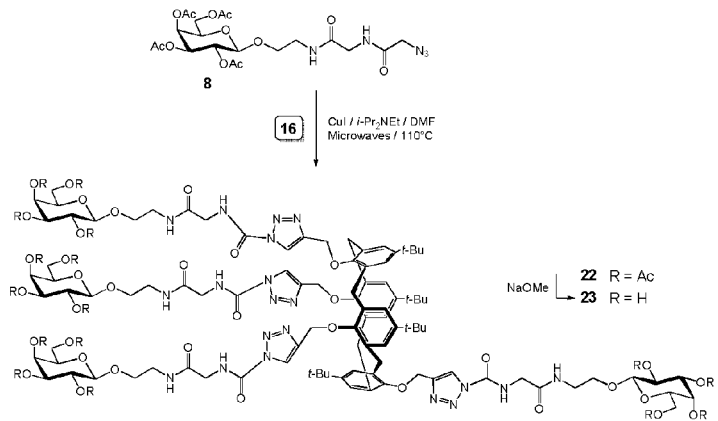
Figure 3B:
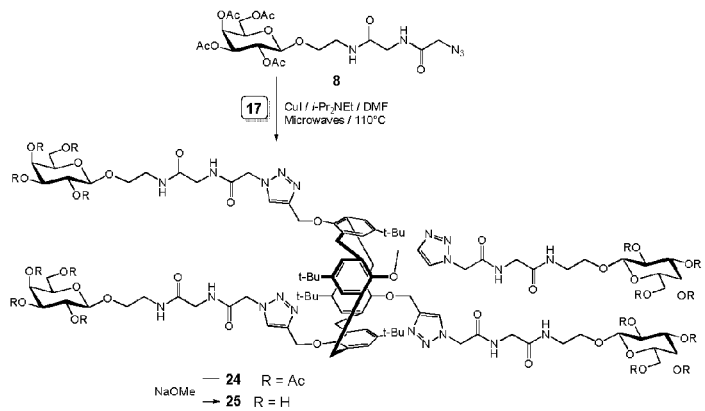
Figure 3C:
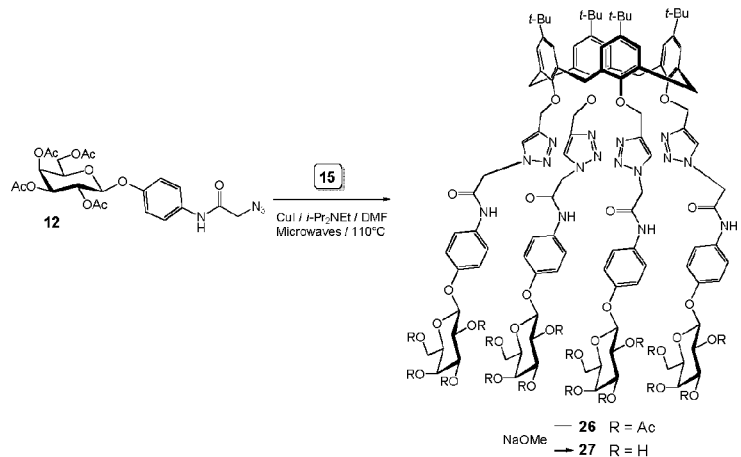
Figure 3C:
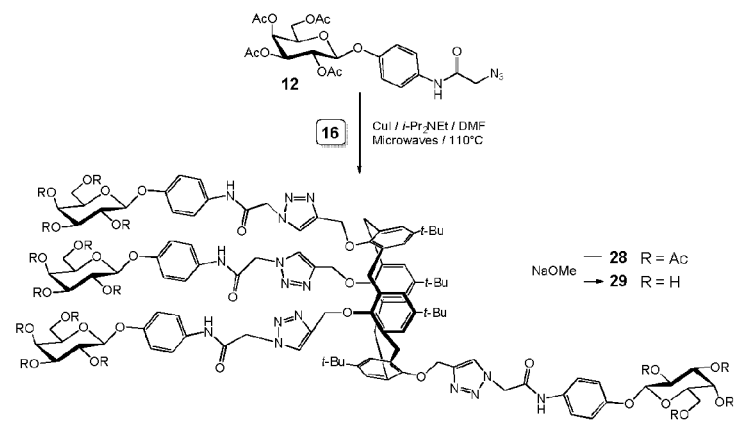
Figure 3C:
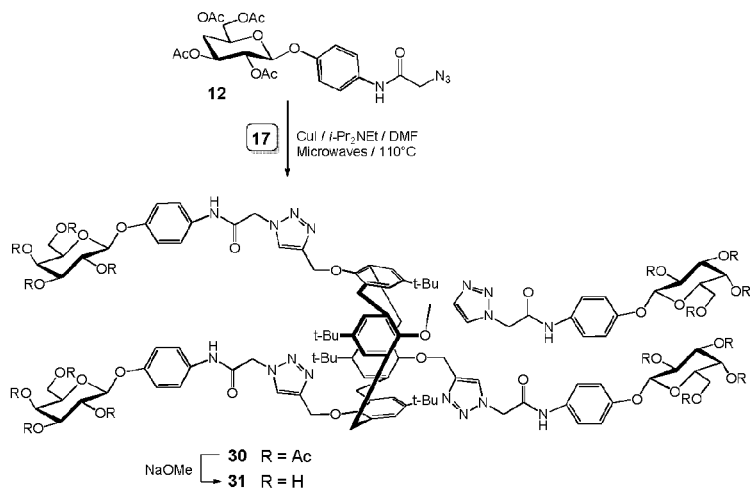

FIG. 3a represents synthesis schemes of tetravalent calixarene-based glycosylated compound (I) named "19" by using the carbohydrate azido-derivatives (III) named "3" prepared as illustrated in FIG. 2. FIG. 3b represent synthesis schemes of glycomimetic (I) respectively named "21" (see FIG. 3b-1), "23" (see FIGS. 3b-2) and "25" (see FIG. 3b-3) by using the carbohydrate azido-derivative "8". FIG. 3c represent synthesis schemes of glycomimetic (I) respectively named "27" (see FIG. 3c-1), "29" (see FIGS. 3c-2) and "31" (see FIG. 3c-3) by using the carbohydrate azido-derivative "12".

Figure 4:
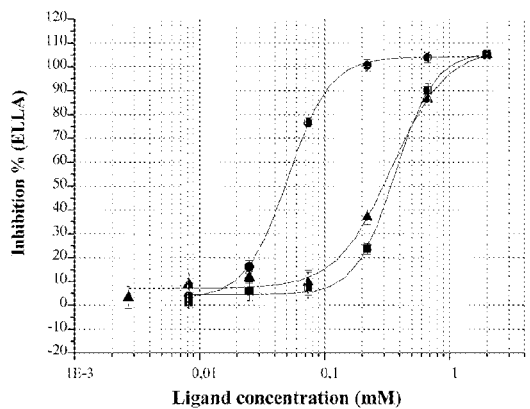

FIG. 4 represents curves for Enzyme-Linked Lectin Assay (ELLA). More particularly this figure illustrates the comparison of the competition effect of three different monovalent glycosylated compounds (I), named respectively 5, 10 and 14. The curve with the symbol ■ represents the compound 5. The curve with the symbol ▲ represents the compound 10. The curve with the symbol ● represents the compound 14.

Figure 5A:
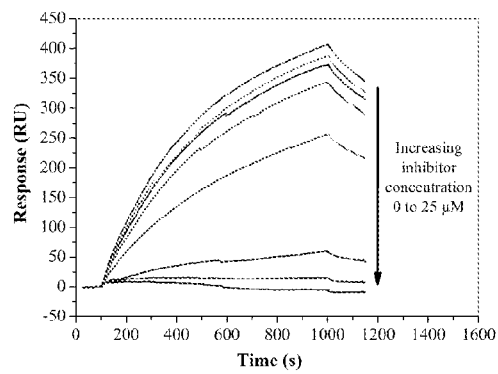
Figure 5B:
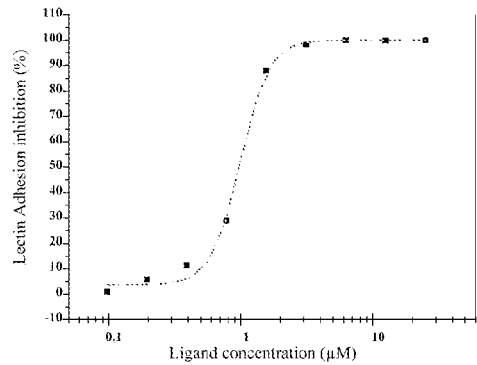

FIGS. 5a and 5b refer to the tetravalent calixarene-based glycosylated compound (I), named 19, for the inhibition of binding of LecA on a galactose-coated chip by SPR. More particularly FIG. 5a represents the sensorgrams obtained with increasing concentrations of compound 19. FIG. 5b represents the inhibition curve derived from the different sensorgrams and used for the calculation of IC50 value.

Figure 6:
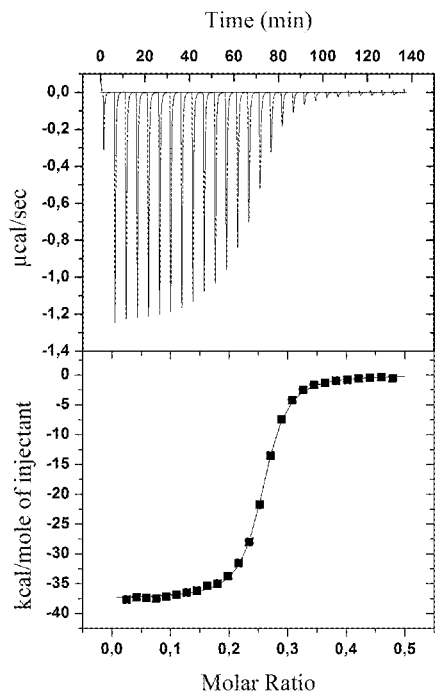

FIG. 6 represents ITC thermogram of the interaction between LecA and glycocompound. The top represents the raw ITC data and the bottom the binding isotherm for the binding of compound 19 to LecA.

Figure 7:
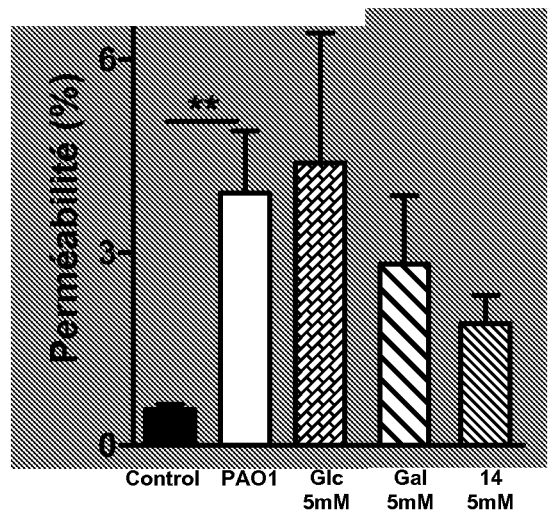

FIG. 7 displays the protective effect of different monosaccharides (glucose, galactose) and derivatives (compound 14) in a mice model with infection by *P. aeruginosa*. The permeability measures the deterioration of the alveolar barrier, i.e. the lung tissue damages caused by the bacterial infection.

EXAMPLE I

Preparation of Calixarene-Based Glycosylated Compound (I)

The general synthesis scheme used in this example for preparing the calixarene-based glycosylated compound of general formula (I) is illustrated in FIGS. 1a and 1b, wherein a propargylated calix[4]arene of formula (IV) is prepared by regioselective multi-propargylation of a calix[4]arene of formula (V) with a propargylated compound of formula (VI), then the said propargylated calix[4]arene of formula (IV) is conjugated with a carbohydrate derivative of formula (III) in order to obtain a acetyl-protected calixarene-based glycosylated compound of formula (II) which leads, when deprotected by hydrolysis, to calixarene-based glycosylated compound (I).

The specific synthetic schemes illustrating the general synthesis scheme are illustrated in FIGS. 2a, 2b and FIGS. 3a, 3b, 3c.

The compounds more particularly prepared here are tetravalent calixarene-based glycosylated compound (I) wherein:

D represents a —$CH_2$— group,
E represents an alkyl group which is the tert-butyl group,
A defined in the B group represents an oxygen atom,
the sugar defined in the C group is the β-D-galactosyl and,
the linker defined in the C group represents respectively:
CO—NH—CH$_2$CH$_2$—O—CH$_2$CH$_2$: see compound "19";
CO—NH—CH$_2$CO—NH—CH$_2$CH$_2$: see compounds "21", "23" and "25";
CO—NH—C$_6$H$_4$: see compounds "27", "29" and "31".
The tetravalent glycomimetics compounds 19, 21, 23, 25, 27, 29 are in the following conformations:
1,3 alternate conformation for glycomimetics 19, 25 and 31,
cone conformation for glycomimetics 21 and 27,
partial cone conformation for glycomimetics 23 and 29.

General experimental methods are now described for preparing these calixarene-based glycosylated compounds 19, 21, 23, 25, 27, 29 and 31.

All reagents for synthesis were commercial (highest purity available for reagent grade compounds) and used without further purification. Solvents were distilled over $CaH_2$ ($CH_2Cl_2$), $Mg/I_2$ (MeOH), Na/benzophenone (THF) or purchased dry. All reactions were performed under an Argon atmosphere. Reactions under microwave activation were performed on a Biotage Initiator system. NMR solvents were purchased from Euriso-Top (Saint Aubin, France).

NMR spectra were recorded at 293 K, unless otherwise stated, using a 300 MHz or a 400 MHz Spectrometer. Shifts are referenced relative to deuterated solvent residual peaks.

The following abbreviations are used to explain the observed multiplicities: s, singlet; d, doublet; t, triplet; q, quadruplet; m, multiplet and bs, broad singlet.

Complete signal assignments from 1D and 2D NMR were based on COSY, HSQC and HMBC correlations.

Infrared spectra were recorded using an FT-IR spectrometer with ATR attachment. High Resolution (LSIMS) mass spectra were recorded in the positive mode using a Thermo Finnigan Mat 95 XL spectrometer.

ESI mass spectra were recorded in the positive mode using a Thermo Finnigan LCQ spectrometer. High resolution (HR-ESI-QTOF) mass spectra were recorded using a Bruker MicrOTOF-Q II XL spectrometer.

MALDI-ToF mass spectra were recorded in positive ion reflectron mode using a Voyager DE-STR spectrometer (Applied Biosystem) with CHCA (φ-cyano-4-hydroxycinnamic acid, 10 $g \cdot L^{-1}$ in MeOH) and NaI (10 $g \cdot L^{-1}$ in acetone) as matrix.

Thin-layer chromatography (TLC) was carried out on aluminum sheets coated with silica gel 60 $F_{254}$ (Merck). TLC plates were inspected by UV light (λ=254 nm) and developed by treatment with a mixture of 10% $H_2SO_4$ in $EtOH/H_2O$ (95:5 v/v) followed by heating.

Silica gel column chromatography was performed with silica gel Si 60 (40-63 μm). Optical rotation was measured using a Perkin Elmer polarimeter.

1) General Procedure for 1,3-Dipolar Cycloadditions (Method A)

Unless otherwise stated, the alkyne-functionalized compound, copper iodide, DIPEA and azido-derivative in degassed DMF were introduced into a Biotage Initiator 2-5 mL vial. The vial was flushed with argon and the solution was sonicated for 30 seconds. The vial was sealed with a septum cap and heated at 110° C. for 15 min under microwave irradiation (solvent absorption level: High). After uncapping the vial, if the product is partially soluble in water, the crude mixture was concentrated and co-evaporated with toluene 3 times before flash chromatography. If the product is not soluble in water at all, the mixture was diluted with EtOAc (250 mL). The organic layer was washed with 150 mL portions of 1N HCl, saturated $NaHCO_3$, water, and brine successively. The organic layer was dried ($Na_2SO_4$), filtered and evaporated. The crude product was purified by flash silica gel column chromatography to afford the desired cycloadducts.

2) General Procedure for Deacetylation (Method B)

Unless otherwise stated, the acetylated glycoside or glycocluster (1 eq.) was suspended in distilled MeOH, ultra-pure water and ultra-pure triethylamine (5:1:1, v/v/v). The mixture was stirred under Argon at room temperature for 2 to 4 days. Solvents were evaporated, co-evaporated with toluene three times and the resulting white foam was dissolved in ultra-pure water (5 mL) and freeze-dried to afford pure glycomimetics.

a) 1-Azido-3-oxapent-5-yl 2,3,4,6-tetra-O-acetyl-β-D-galactopyranoside ("2")

$SnCl_4$ (1M in $CH_2Cl_2$, 15.4 mL, 15.4 mmol, 3 eq.) was added dropwise (within 60 min-syringe pump) at room temperature to a stirred solution of 1 (2 g, 5.1 mmol), silver trifluoroacetate (1.7 g, 7.7 mmol, 1.5 eq.) and 2-(2-chloroethoxy)ethanol (0.957 g, 7.7 mmol, 1.5 eq.) in freshly distilled dichloromethane (60 mL). The mixture was protected from light. Disappearance of the starting material was observed (TLC monitoring) 10 minutes after all $SnCl_4$ was added. The mixture was transferred in saturated aqueous $NaHCO_3$ (400 mL) and the pH was checked to be up to 8. The solution was vigorously stirred for 15 min. The biphasic solution was extracted with $CH_2Cl_2$ (3×150 mL). The organic layers were combined, washed successively with saturated aqueous $NaHCO_3$ (2×150 mL), water (2×150 mL), brine (150 mL) and dried ($Na_2SO_4$). After concentration and total removal of $CH_2Cl_2$ with high vacuum, the crude product (pale yellow gum) was dissolved in anhydrous DMF (50 mL). Sodium azide (1.66 g, 25.6 mmol, 5 eq.) and tetra-n-butyl ammonium iodide (0.378 g, 1.0 mmol, 0.2 eq.) was added, and the mixture was stirred at 80° C. under argon for 16 hrs. The mixture was cooled to r.t., filtered and the solid was washed with EtOAc. The filtrate was diluted with EtOAc to reach a total volume of 400 mL. The organic layer was washed with aq. $NaHCO_3$ (2×100 mL), water (2×100 mL), brine (100 mL) and dried. After concentration, the residue (yellow to orange gum) was purified by silica gel column chromatography (PE/EtOAc, 6:4) to afford the corresponding azido-functionalized β-glycoside 2 as a colorless gum (1.348 g, 57% over 2 steps). $R_f$=0.31 (PE:EtOAc, 6:4). $[\alpha]_D$=−3.9° (c=1, $CH_2Cl_2$).

b) 1-Azidoacetamido-3-oxapent-5-yl 2,3,4,6-tetra-O-acetyl-β-D-galactopyranoside ("3")

In a 100 mL round-bottom flask containing 2 (0.951 g, 2.06 mmol) was added 40 mL of freshly distilled $CH_2Cl_2$ under argon. The mixture was degassed with 3 vacuum/argon cycles. Then, 0.219 mg (0.21 mmol, 0.1 eq.) of Pd/C (10 wt %) was added and the mixture was submitted to 3 others vacuum/argon cycles. The solution was subjected to hydrogen atmosphere by 3 vacuum/hydrogen cycles and stirred at r.t. for 20 hrs. The reduction of the azido moiety can be monitored by TLC (EtOAc). If some starting material is still present after 20 hrs, Pd/C could be added after flushing the flask with argon. After 3 vacuum/hydrogen cycles, the mixture could be stirred at r.t. for few more hours. After total disappearance of starting material, the mixture was flushed with argon and $Et_3N$ (575 μL, 4.12 mmol, 2 eq.) was added. Bromoacetylbromide (214 μL, 2.47 mmol, 1.2 eq.) was added dropwise and the mixture was stirred for 12 hrs. The mixture was filtered through a plug of celite ($CH_2Cl_2$) to remove Pd/C. The crude mixture in $CH_2Cl_2$ (250 mL) was washed with HCl 1N (2×100 mL), saturated $NaHCO_3$ (2×100 mL), water (2×100 mL) and brine (100 mL). After drying ($Na_2SO_4$), concentration and total removal of $CH_2Cl_2$ with high vacuum, the crude product (pale orange gum) was dissolved in anhydrous DMF (30 mL). Sodium azide (0.67 g, 10.3 mmol, 5 eq.) and tetra-n-butyl ammonium iodide (0.152 g, 0.41 mmol, 0.2 eq.) was added, and the mixture was stirred at 80° C. under argon for 16 hrs. The mixture was cooled to r.t., filtered and the solid was washed with EtOAc. The filtrate was diluted with EtOAc to reach a total volume of 300 mL. The organic layer was washed with aq. NaHCO$_3$ (2×100 mL), water (2×100 mL), brine (100 mL) and dried. After concentration, the residue (orange gum) was purified by silica gel column chromatography (EtOAc) to afford the azido-functionalized glycoside 3 as a colorless gum (590 mg, 57% over 3 steps).

R$_f$=0.37 (EtOAc). [α]$_D$=−13.3° (c=1, CH$_2$Cl$_2$).

HR-ESI-QTOF MS (positive mode) m/z: calcd for C$_{20}$H$_{30}$N$_4$NaO$_{12}$ [M+Na]$^+$ 541.1752. found 541.1744. calcd for C$_{20}$H$_{30}$N$_2$NaO$_{12}$ [M+Na−N$_2$]$^+$ 513.1691. found 513.1688.

c) 1-[(1,2,3-Triazol-4-acetoxymethyl-1-yl)-acetamido]-3-oxapent-5-yl 2,3,4,6-tetra-O-acetyl-β-D-galactopyranoside ("4")

Obtained as a white foam (136 mg, 72%) following Method A: 3 (158 mg, 0.30 mmol, 1 eq.), propargyl acetate (45 mg, 0.46 mmol, 1.5 eq.), copper iodide (5.8 mg, 0.1 eq.) and DIPEA (159 μL, 3 eq.) in DMF (3 mL). The mixture was worked up, aqueous layer was extracted with CH$_2$Cl$_2$ and the crude product was purified on silica gel (EtOAc) to afford the pure compound 4.

R$_f$=0.16 (EtOAc).
[α]$_D$=−30.8° (c=0.4, CH$_2$Cl$_2$).
HR-ESI-QTOF MS (positive mode) m/z: calcd for C$_{25}$H$_{36}$N$_4$NaO$_{14}$ [M+Na]$^+$ 639.2120. found 639.2096.

d) 1-[(1,2,3-Triazol-4-hydroxymethyl-1-yl)-acetamido]-3-oxapent-5-yl β-D-galactopyranoside Obtained as a colorless oil (72 mg, 94%) following Method B: 4 (117 mg, 1 eq.), MeOH (2 mL), water (0.5 mL) and triethylamine (0.5 mL).

[α]$_D$=+2.9° (c=0.45, H$_2$O).
HR-ESI-QTOF MS (positive mode) m/z: calcd for C$_{15}$H$_{26}$N$_4$NaO$_9$ [M+Na]$^+$ 429.1586. found 429.1592.

e) 2-Azidoethyl 2,3,4,6-tetra-O-acetyl-β-D-galactopyranoside ("6")

SnCl$_4$ (1M in CH$_2$Cl$_2$, 38.4 mL, 38.4 mmol, 3 eq.) was added dropwise (within 120 min syringe pump) at room temperature to a stirred solution of 1 (5 g, 12.8 mmol), silver trifluoroacetate (4.2 g, 19.2 mmol, 1.5 eq.) and 2-chloroethanol (1.3 mL, 19.2 mmol, 1.5 eq.) in freshly distilled dichloromethane (150 mL). The mixture was protected from light. Disappearance of the starting material could not be observed as starting material and desired compound have the same R$_f$. After 3 hours (1 hour after the end of SnCl$_4$ addition), the mixture was transferred in saturated aqueous NaHCO$_3$ (750 mL) and the pH was checked to be up to 8. The solution was vigorously stirred for 20 min. The biphasic solution was extracted with CH$_2$Cl$_2$ (3×150 mL). The organic layers were combined, washed successively with saturated aqueous NaHCO$_3$ (2×150 mL), water (2×150 mL), brine (150 mL) and dried (Na$_2$SO$_4$). After concentration and total removal of CH$_2$Cl$_2$ with high vacuum, the crude product (pale yellow gum) was dissolved in anhydrous DMF (80 mL). Sodium azide (4.3 g, 66.3 mmol, 5 eq.) and tetra-n-butyl ammonium iodide (0.491 g, 1.3 mmol, 0.1 eq.) was added, and the mixture was stirred at 70° C. under argon for 16 hrs. The mixture was cooled to r.t., filtered and the solid was washed with EtOAc. The filtrate was diluted with EtOAc to reach a total volume of 400 mL. The organic layer was washed with aq. NaHCO$_3$ (2×100 mL), water (2×100 mL), brine (100 mL) and dried. After concentration, the residue (yellow oil) was purified by silica gel column chromatography (PE/EtOAc, 1:1) to afford the corresponding azido-functionalized β-glycoside 6 as a colorless gum (4.186 g, 78% over 2 steps).

R$_f$=0.46 (PE:EtOAc, 1:1).

f) 2-[(N-Chloroacetyl)glycinamido]-ethyl 2,3,4,6-tetra-O-acetyl-β-D-galactopyranoside ("7")

In a 250 mL round-bottom flask containing 6 (3.875 g, 9.28 mmol) was added 150 mL of freshly distilled CH$_2$Cl$_2$ under argon. The mixture was degassed with 3 vacuum/argon cycles. Then, 0.495 mg (0.46 mmol, 0.05 eq.) of Pd/C (10 wt %) was added and the mixture was submitted to 3 others vacuum/argon cycles. The solution was subjected to hydrogen atmosphere by 3 vacuum/hydrogen cycles and stirred at r.t. for 20 hrs. The reduction of the azido moiety can be monitored by TLC (PE/EtOAc, 1:1). After total disappearance of starting material, the mixture was flushed with argon and filtered through a plug of celite (CH$_2$Cl$_2$) to remove Pd/C. The crude mixture was concentrated under vacuum yielding grey foam. In a second 250 mL round-bottom flask containing N-chloroacetylglycine (2.11 g, 13.9 mmol, 1.5 eq.), anhydrous DMF (45 mL) and distilled CH$_2$Cl$_2$ (50 mL) were added under argon. The mixture was cooled to −10° C. using a NaCl/ice bath, then HOBt (2.51 g, 18.6 mmol, 2 eq.) and EDCI (2.81 g, 18.6 mmol, 2 eq.) were added. The mixture was stirred for 40 minutes then a solution of the crude amine in 55 mL of CH$_2$Cl$_2$ was added dropwise (within 2 hrs). The reaction was allowed to warm up at r.t. and stirred at r.t. for 16 hrs. The crude mixture was then concentrated, diluted in EtOAc (400 mL) and washed with HCl 1N (2×100 mL), saturated NaHCO$_3$ (2×100 mL), water (2×100 mL) and brine (100 mL). After drying (Na$_2$SO$_4$) and concentration, the residue was purified by silica gel column chromatography (EtOAc) to afford the chloro-functionalized glycoside 7 as white foam (2.612 g, 54% over 2 steps).

R$_f$=0.30 (EtOAc). [α]$_D$=+8.2° (c=1, CH$_2$Cl$_2$).
ESI-MS (positive mode) m/z: 547.1 [M+Na], 1070.3 [2M+Na]$^+$ HR-ESI-MS (positive mode) m/z: calcd for C$_{20}$H$_{29}$ClN$_2$NaO$_{12}$ [M+Na]$^+$ 547.1307. found 547.1306.

g) 2-[(N-Azidoacetamido)glycinamido]-ethyl 2,3,4,6-tetra-O-acetyl-β-D-galactopyranoside ("8")

In a 100 mL round-bottom flask containing chloro-derivative 7 (2.535 g, 4.8 mmol), sodium azide (1.57 g, 24.1 mmol, 5 eq.) and tetra-n-butyl ammonium iodide (0.355 g, 1.0 mmol, 0.2 eq.), anhydrous DMF (40 mL) was added. The mixture was stirred at 80° C. under argon for 16 hrs. TLC did not allow monitoring of the reaction as starting material and desired compound have similar polarity. The mixture was cooled to r.t., filtered and the solid was washed with EtOAc. The filtrate was diluted with EtOAc to reach a total volume of 400 mL. The organic layer was washed with aq. NaHCO$_3$ (2×100 mL), water (2×100 mL), brine (100 mL) and dried (Na$_2$SO$_4$). After concentration, the residue (yellow oil) was purified by silica gel flash chromatography (EtOAc) to afford the corresponding azido-functionalized glycoside 8 as a white foam (2.00 g, 78%).

R$_f$=0.30 (EtOAc). [α]$_D$=+3.0° (c=1, CH$_2$Cl$_2$).
HR-ESI-QTOF MS (positive mode) m/z: calcd for C$_{20}$H$_{29}$N$_5$NaO$_{12}$ [M+Na]$^+$ 554.1705. found 554.1715.

h) 2-N-[(1,2,3-Triazol-4-acetoxymethyl-1-yl)-acetamido]glycinamido-ethyl 2,3,4,6-tetra-O-acetyl-β-D-galactopyranoside ("9")

Obtained as a white foam (176 mg, 99%) following Method A: 8 (150 mg, 0.28 mmol, 1 eq.), propargyl acetate (41 mg, 0.42 mmol, 1.5 eq.), copper iodide (5.3 mg, 0.1 eq.) and DIPEA (146 µL, 3 eq.) in DMF (3 mL). The crude mixture was evaporated off and co-evaporated 3 times with toluene. Resulting crude product 9 was purified on silica gel (EtOAc then EtOAc/MeOH, 9:1) by two successive flash chromatographies yielding pure compound.

$R_f$=0.50 (EtOAc/MeOH, 9:1). $[\alpha]_D$=+4.3° (c=1.1, $CH_2Cl_2$).

HR-ESI-QTOF MS (positive mode) m/z: calcd for $C_{25}H_{35}N_5NaO_{14}$ [M+Na]$^+$ 652.2073. found 652.2076.

i) 2-N-[(1,2,3-Triazol-4-hydroxymethyl-1-yl)-acetamido]glycinamido-ethyl β-D-galactopyranoside ("10")

Obtained as a white freeze-dried powder (82 mg, 78%) following Method B: 9 (160 mg, 1 eq.), MeOH (5 mL), water (1 mL) and triethylamine (1 mL). After stirring at r.t. for 2 days and concentration, the mixture was dissolved in ultra-pure water (5 mL) then freeze-dried to afford the pure deacetylated glycoside 10.

$[\alpha]_D$=+4.2° (c=0.55, $H_2O$).

HR-ESI-QTOF MS (positive mode) m/z: calcd for $C_{15}H_{25}N_5NaO_9$ [M+Na]$^+$ 442.1540. found 442.1544.

j) 4-(Azidoacetamido)phenyl 2,3,4,6-tetra-O-acetyl-β-D-galactopyranoside ("12")

In a 250 mL round-bottom flask containing 11 (4.07 g, 13.51 mmol) and DMAP (20 mg) was added 50 mL of pyridine under argon. Then, 35 mL of $Ac_2O$ was added dropwise. The mixture was stirred at r.t. for 16 hrs. The crude mixture was diluted in EtOAc (800 mL) and washed with HCl 1N (2×300 mL), saturated $NaHCO_3$ (2×300 mL), water (2×300 mL) and brine (300 mL). After drying ($Na_2SO_4$) and concentration, the residue crystallized from PE and was filtered and dried to afford 5.75 g of the pure acetylated intermediate (91%). Then, in a 1 L round-bottom flask containing the acetylated p-nitrophenyl-galactopyranoside, freshly distilled $CH_2Cl_2$ was added under argon atmosphere. The mixture was degassed with 3 vacuum/argon cycles. Then, 0.634 mg (0.60 mmol, 0.05 eq.) of Pd/C (10 wt %) was added and the mixture was submitted to 3 others vacuum/argon cycles. The solution was subjected to hydrogen atmosphere by 3 vacuum/hydrogen cycles and stirred at r.t. for 16 hrs. The reduction of the nitro group can be monitored by TLC (PE/EtOAc, 1:1). After total disappearance of starting material, the mixture was flushed with argon, cooled to 0° C., and $Et_3N$ (2.0 mL, 14.32 mmol, 1.2 eq.) was added. Bromoacetylbromide (1.24 mL, 14.32 mmol, 1.2 eq.) was added dropwise and the mixture was stirred for 1 hr at 0° C. The mixture was allowed to warm up at r.t. for 1 h and was filtered through a plug of celite ($CH_2Cl_2$) to remove Pd/C. The crude mixture in $CH_2Cl_2$ (600 mL) was washed with HCl 1N (2×250 mL), water (2×250 mL) and brine (250 mL). After drying ($Na_2SO_4$), concentration and total removal of $CH_2Cl_2$ with high vacuum, the crude bromide derivative (pale yellow solid) was dissolved in anhydrous DMF (80 mL). Sodium azide (4.1 g, 62.6 mmol, 5 eq.) and tetra-n-butyl ammonium iodide (0.46 g, 1.25 mmol, 0.1 eq.) was added, and the mixture was stirred at 50° C. under argon for 16 hrs. The mixture was cooled to r.t., filtered and the solid was washed with EtOAc. The filtrate was diluted with EtOAc to reach a total volume of 600 mL. The organic layer was washed with aq. $NaHCO_3$ (2×200 mL), water (2×200 mL), brine (200 mL) and dried. After concentration, the residue (pale yellow solid) was purified by silica gel column chromatography (PE/EtOAc, 1:1) followed by crystallization ($CH_2Cl_2$/PE) to afford the azido-functionalized glycoside 12 as a white solid (5.229 g, 74% over 4 steps).

$R_f$=0.29 (PE/EtOAc, 1:1). $[\alpha]_D$=+6.6° (c=1.3, $CH_2Cl_2$).

ESI-MS (positive mode) m/z: 545.0 [M+Na]$^+$, 1066.4 [2M+Na]$^+$ HR-ESI-MS (positive mode) m/z: calcd for $C_{22}H_{26}N_4NaO_{11}$ [M+Na]$^+$ 545.1496. found 545.1496.

k) 4-[(1,2,3-Triazol-4-acetoxymethyl-1-yl)-acetamido]phenyl 2,3,4,6-tetra-O-acetyl-β-D-galactopyranoside ("13")

Obtained as a white foam (350 mg, 98%) following Method A: 12 (300 mg, 0.57 mmol, 1 eq.), propargyl acetate (84 mg, 0.86 mmol, 1.5 eq.), copper iodide (10.9 mg, 0.1 eq.) and DIPEA (300 µL, 3 eq.) in DMF (4 mL). The crude mixture was diluted in EtOAc (300 mL) and the organic layer was washed with HCl 1N (2×100 mL), saturated $NaHCO_3$ (2×100 mL), water (2×100 mL) and brine (100 mL). After drying ($Na_2SO_4$) and concentration, the residue was purified by silica gel (EtOAc) flash chromatography yielding pure compound 13.

$[\alpha]_D$=+8.2° (c=1, $CH_2Cl_2$).

ESI-MS (positive mode) m/z: 621.1 [M+H]$^+$, 643.0 [M+Na], 1262.3 [2M+Na]$^+$ HR-ESI-QTOF-MS (positive mode) m/z: calcd for $C_{27}H_{32}N_4NaO_{13}$ [M+Na]$^+$ 643.1841. found 643.1858.

l) 4-[(1,2,3-Triazol-4-hydroxymethyl-1-yl)-acetamido]phenyl β-D-galactopyranoside ("14")

Obtained as a white freeze-dried powder (206 mg, 95%) following Method B: 13 (335 mg, 1 eq.), MeOH (10 mL), water (2 mL) and triethylamine (2 mL). After stirring at r.t. for 2 days and concentration, the mixture was dissolved in ultra-pure water (5 mL) then freeze-dried to afford the pure deacetylated glycoside 14.

$[\alpha]_D$=−18.8° (c=0.43, $H_2O$)

ESI-MS (positive mode) m/z: 433.1 [M+Na]. ESI-MS (negative mode) m/z: 409.1 [M−H]$^−$, 433.1 [M+Cl]$^−$. HR-ESI-QTOF-MS (positive mode) m/z: calcd for $C_{17}H_{22}N_4NaO_8$ [M+Na]$^+$ 433.1330. found 433.1324.

m) Glycomimetic ("18")

Obtained as a white foam (154 mg, 89%) following Method A: 17 (48 mg, 60.1 µmol, 1 eq.) 3 (187 mg, 361 µmol, 6 eq.), copper iodide (6 mg, 30 µmol, 0.5 eq.) and DIPEA (52 µL, 300 µmol, 5 eq.). Purified by silica gel flash chromatography (EtOAc:MeOH, 1:0 then 95:5).

$R_f$=0.45 (EtOAc:MeOH, 95:5). $[\alpha]_D$=−2.5 (c=1.26, $CH_2Cl_2$).

HR-ESI-QTOF MS (positive mode): m/z calcd for $C_{136}H_{185}N_{16}O_{52}$ [M+H]$^+$ 2874.2318. found 2874.2306. calcd for $C_{136}H_{186}N_{16}O_{52}$ [M+2H]$^{++}$1437.6196. found 1437.6260.

n) Glycomimetic ("19")

Obtained as a white foam (108 mg, 99%) following Method B: 18 (142 mg, 1 eq.), MeOH (2 mL), water (0.5 mL) and triethylamine (0.5 mL). After stirring at r.t. for 2 days and concentration, the mixture was dissolved in ultra-pure water (5 mL) then freeze-dried to afford the pure deacetylated glycoside 19.

$[\alpha]_D$=−0.5 (c=1.1/DMSO).

HR-ESI-QTOF MS (positive mode): m/z calcd for $C_{104}H_{152}N_{16}Na_2O_{36}$ [M+2Na]$^{++}$ 1123.5170. found 1123.5226.

o) Glycomimetic ("20")

Obtained as a white foam (103 mg, 56%) following Method A: 15 (50 mg, 63 μmol, 1 eq.) 8 (200 mg, 380 μmol, 6 eq.), copper iodide (6 mg, 31 μmol, 0.5 eq.) and DIPEA (54 μL, 310 μmol, 5 eq.). Microwave irradiation: 35 min., 110° C. Without workup, crude mixture is concentrated, co-evaporated with toluene and purified by silica gel flash chromatography (CHCl$_3$:MeOH, 1:0 then 9:1).

$R_f$=0.01 (EtOAc:MeOH, 9:1). [α]$_D$=−1.2 (c=1.0, CH$_2$Cl$_2$).
HR-ESI-QTOF-MS (positive mode) m/z: calcd for $C_{136}H_{182}N_{20}O_{52}$ [M+2H]$^{++}$1463.6100. found 1463.6159. calcd for $C_{136}H_{181}KN_{20}O_{52}$ [M+H+K]$^{++}$ 1482.5880. found 1482.5885.

p) Glycomimetic ("21")

Obtained as a white foam (72 mg, 92%) following Method B: 20 (102 mg, 1 eq.), MeOH (2 mL), water (1 mL) and triethylamine (1 mL). After stirring at r.t. for 3 day and concentration, the mixture was dissolved in ultra-pure water (5 mL) then freeze-dried to afford the pure deacetylated glycoside 21.

[α]$_D$=−0.4 (c=0.68/DMSO).
HR-ESI-QTOF-MS (positive mode) m/z: calcd for $C_{104}H_{149}N_{20}O_{36}$ [M+H]$^+$ 2254.0438. found 2254.0430. calcd for $C_{104}H_{148}N_{20}Na_2O_{36}$ [M+2Na]$^{++}$1149.5075. found 1149.5126. calcd for $C_{104}H_{150}N_{20}O_{36}$ [M+2H]$^{++}$ 1127.5255. found 1127.5309.

q) Glycomimetic ("22")

Obtained as a white foam (111 mg, 81%) following Method A: 16 (37.7 mg, 47 μmol, 1 eq.) 8 (142 mg, 282 μmol, 5.7 eq.), copper iodide (2.5 mg, 23 μmol, 0.5 eq.) and DIPEA (41 μL, 235 μmol, 5 eq.) in DMF (2.5 mL). Microwave irradiation: 30 min., 110° C. Without workup, crude mixture is concentrated, co-evaporated with toluene and purified by silica gel flash chromatography (DCM:MeOH, 1:0 then 85:15).

$R_f$=0.4 (EtOAc:MeOH, 90:10).
[α]$_D$=−0.9 (c=1.0, CH$_2$Cl$_2$).
HR-ESI-QTOF-MS (positive mode) m/z: calcd for $C_{136}H_{180}N_{20}Na_2O_{52}$ [M+2Na]$^{++}$ 1485.5920. found 1485.5934.

r) Glycomimetic ("23")

Obtained as a white foam (102 mg, 79%) following Method B: 22 (166 mg, 1 eq.), MeOH (2 mL), water (1 mL) and triethylamine (1 mL). After stirring at r.t. for 1 day and concentration, the mixture was co-evaporated three times in toluene, precipitated from H2O, MeOH, acetone. After filtration, the compound was dissolved in ultra-pure water (5 mL) then freeze-dried to afford the pure deacetylated glycoside 23.

[α]$_D$=−1.5 (c=1.14, DMSO).
HR-ESI-QTOF-MS (positive mode) m/z: calcd for $C_{104}H_{149}KN_{20}O_{36}$ [M+H+K]$^{++}$ 1146.5035. found 1146.5028.

s) Glycomimetic ("24")

Obtained as a white foam (110 mg, 59%) following Method A: 17 (50 mg, 63 μmol, 1 eq.) 2 (200 mg, 380 μmol, 6 eq.), copper iodide (6 mg, 31 μmol, 0.5 eq.) and DIPEA (54 μL, 310 μmol, 5 eq.). Microwave irradiation: 15 min., 110° C. Without workup, crude mixture is concentrated, co-evaporated with toluene and purified by silica gel flash chromatography (EtOAc:MeOH, 1:0 then 9:1). A second flash chromatagrophy sometimes could be required (CHCl$_3$:MeOH, 1:0 then 95:5).

$R_f$=0.52 (EtOAc:MeOH, 9:1).
[α]$_D$=+1.5 (c=1.0, CH$_2$Cl$_2$).
HR-ESI-QTOF-MS (positive mode) m/z: calcd for $C_{136}H_{180}N_{20}NaO_{52}$ [M+H]$^+$ 2948.1948. found 2498.1957. calcd for $C_{136}H_{180}N_{20}Na_2O_{52}$ [M+2Na]$^+$1485.5920. found 1485.5954.

t) Glycomimetic ("25")

Obtained as a white foam (76 mg, 90%) following Method B: 24 (112 mg, 1 eq.), MeOH (2 mL), water (0.5 mL) and triethylamine (0.5 mL). After stirring at r.t. for 3 day and concentration, the mixture was co-evaporated three times in toluene, precipitated from MeOH/Et$_2$O acetone. After filtration, the compound was dissolved in ultra-pure water (5 mL) then freeze-dried to afford the pure deacetylated glycoside 25.

HR-ESI-QTOF-MS (positive mode) m/z: calcd for $C_{104}H_{150}N_{20}O_{36}$ [M+2H]$^{++}$1127.5255. found 1127.5322. calcd for $C_{104}H_{148}N_{20}Na_2O_{36}$ [M+2Na]$^{++}$1149.5075. found 1149.5134. calcd for $C_{104}H_{149}N_{20}O_{36}$ [M+H]$^+$ 2254.0438. found 2254.0513.

u) Glycomimetic ("26")

Obtained as a white foam (253 mg, 70%) following Method A: 15 (100 mg, 0.125 mmol, 1 eq.) 12 (391 mg, 0.749 mmol, 6 eq.), copper iodide (12 mg, 62 μmol, 0.5 eq.) and DIPEA (109 μL, 0.624 mmol, 5 eq.). Microwave irradiation: 45 min., 110° C. Purified by silica gel flash chromatography (PE:EtOAc, 4:6 then EtOAc, then EtOAc:MeOH, 95:5).

[α]$_D$=+1.5 (c=0.68, CH$_2$Cl$_2$).
MALDI-TOF MS (positive ion reflectron mode): calcd for $C_{144}H_{168}N_{16}NaO_{48}$ [M+Na]$^+$ 2912.11. found 2912.03.

v) Glycomimetic ("27")

Obtained as a white foam (129 mg, 81%) following Method B: 26 (207 mg, 1 eq.), MeOH (10 mL), water (2 mL) and triethylamine (2 mL). After stirring at r.t. for 1 day and concentration, the mixture was co-evaporated three times in toluene. The compound was dissolved in ultra-pure water (5 mL) then freeze-dried to afford the pure deacetylated glycoside 27.

MALDI-TOF MS (positive ion reflectron mode): calcd for $C_{112}H_{136}N_{16}NaO_{32}$ [M+Na]$^+$ 2239.94. found 2239.84.

w) Glycomimetic ("28")

Obtained as a white foam (271 mg, 75%) following Method A: 16 (100 mg, 0.125 mmol, 1 eq.) 12 (391 mg, 0.749 mmol, 6 eq.), copper iodide (12 mg, 62 μmol, 0.5 eq.) and DIPEA (109 μL, 0.624 μmol, 5 eq.). Microwave irradiation: 15 min., 110° C. Purified by silica gel flash chromatography (PE:EtOAc, 4:6 then EtOAc, then EtOAc:MeOH, 95:5).

[α]$_D$=+3.2 (c=1.45, CH$_2$Cl$_2$).
MALDI-TOF MS (positive ion reflectron mode): calcd for $C_{144}H_{168}N_{16}NaO_{48}$ [M+Na]$^+$ 2912.11. found 2912.20.

x) Glycomimetic ("29")

Obtained as a white foam (124 mg, 78%) following Method B: 28 (207 mg, 1 eq.), MeOH (4 mL), water (1 mL)

and triethylamine (1 mL). After stirring at r.t. for 3 day and concentration, the mixture was co-evaporated three times in toluene. The compound was dissolved in ultra-pure water (5 mL) then freeze-dried to afford the pure deacetylated glycoside 29.

$[\alpha]_D = -7.1$ (c=1.15, DMSO).

HR-ESI-QTOF-MS (positive mode) m/z: calcd for $C_{112}H_{137}N_{16}NaO_{32}$ $[M+H+N]^{++}$ 1120.4736. found 1120.4744. calcd for $C_{112}H_{137}KN_{16}O_{32}$ $[M+H+K]^{++}$ 1128.4605. found 1128.4605. calcd for $C_{112}H_{136}KN_{16}NaO_{32}$ $[M+K^+ Na]^{++}$ 1139.4515. found 1139.4527.

y) Glycomimetic ("30")

Obtained as a white foam (307 mg, 85%) following Method A: 17 (100 mg, 0.125 mmol, 1 eq.) 12 (391 mg, 0.749 mmol, 6 eq.), copper iodide (12 mg, 62 µmol, 0.5 eq.) and DIPEA (109 µL, 0.624 mmol, 5 eq.). Microwave irradiation: 15 min., 110° C. Purified by silica gel flash chromatography (PE:EtOAc, 4:6 then EtOAc, then EtOAc:MeOH, 95:5).

$[\alpha]_D = +8.1$ (c=0.80, $CH_2Cl_2$).

MALDI-TOF MS (positive ion reflectron mode): calcd for $C_{144}H_{168}N_{16}NaO_{48}$ $[M+Na]^+$ 2912.11. found 2912.10.

z) Glycomimetic ("31")

Obtained as a white foam (150 mg, 73%) following Method B: 30 (268 mg, 1 eq.), MeOH (10 mL), water (2 mL) and triethylamine (2 mL). After stirring at r.t. for 1 day and concentration, the mixture was co-evaporated three times in toluene. The compound was dissolved in ultra-pure water (5 mL) then freeze-dried to afford the pure deacetylated glycoside 31.

$[\alpha]_D = -9.0$ (c=0.77, DMSO).

EXAMPLE II

Use of the Calixarene-Based Glycosylated Compound (I) for Inhibiting the Binding to Natural Glycoconjugates Present on Cells 1) Experimental Conditions In order to evaluate the in vitro potential of calixarene-based glycosylated compound (I) to inhibit the binding to natural glycoconjugates present on cell, four different methods have been applied which are described below.

Method (1)

Inhibition of Hemagglutination (IHA) (or Hemagglutination Inhibition Assays (HIA)).

The LecA lectin agglutinates red blood cells since they are covered by glycoconjugates. The glycomimetics inhibit this agglutination.

For each compound the minimum concentration able to perform inhibition has been evaluated. The method is not very quantitative but mimics natural system.

More particularly, hemagglutination inhibition assays were performed in U-shaped 96-well microtitre plates. Rabbit erythrocytes were bought from Biomerieux and used without further washing. The erythrocytes were diluted to a 4% solution in NaCl (150 mM). Lectin solutions of 2 mg/mL were prepared in Tris/HCl 20 mM, NaCl 100 mM and $CaCl_2$ 100 µM. The hemagglutination unit (HU) was first obtained by the addition of 25 µL of the 4% erythrocyte solution to 25 µL aliquots of sequential (two-fold) lectin dilutions. The mixture was incubated at 25° C. for 60 minutes. The HU was measured as the minimum lectin concentration required to prevent hemagglutination. For the following lectin-inhibition assays, lectin concentrations of four times that of the hemagglutination unit were used, i.e. a concentration of 6 µg/mL for LecA. Subsequent assays were then carried out by the addition of 12.5 µL lectin solution (at the required concentration) to 25 µL of sequential dilutions of glycoclusters, monomer molecules and controls. These solutions were then incubated at 25° C. for 2 h then 12.5 µL of 4% erythrocyte solution was added followed by an additional incubation at 25° C. for 30 minutes. The minimum inhibitory concentration for each molecule was determined by simple eye detection.

Compounds 5, 10, 14, 19, 21, 23, 25, 27, 29 and 31 were evaluated towards LecA according to Method 1.

Method (2)

Enzyme-Linked Lectin Assay (ELLA) Experiments 96-well plates are covered with polymer presenting galactose (which is the monosaccharide that is bound by LecA). The lectin labelled with biotin is added in presence of competing glycomimetics. IC50 can be measured.

More particularly, ELLA experiments were conducted using 96-well microtitre plates (Nunc Maxisorb) coated with polymeric β-D-galactose (5 µg/mL; Lectinity Holding, Inc., Moscow) diluted in carbonate buffer, pH 9.6 (100 µL) for 1 h at 37° C. After blocking at 37° C. for 1 h with 100 µL per well of 3% (w/v) BSA in PBS, plates were incubated at 37° C. for 1 h with 100 µL of biotinylated LecA at 0.1 µg/mL in the presence of serial dilutions of inhibitors. After washing with T-PBS (PBS containing 0.05% Tween), 100 µL of streptavidin-peroxidase conjugate (dilution 1:10000; Boehringer-Mannheim) was added and left for 1 h at 37° C. The color was developed using 100 µL per well of 0.05 M phosphate/citrate buffer containing O-phenylenediamine dihydrochloride (0.4 mg/mL) and urea hydrogen peroxide (0.4 mg/mL) (Sigma-Aldrich). The reaction was stopped by the addition of 50 µL of 30% H2SO4. Absorbance was read at 490 nm using a microtitre plate reader (Bio-Rad; model 680).

Method (3)

Surface Plasmon Resonance (SPR).

Equivalent method, but performed in miniaturized channel on a galactose-containing chips in a more sophisticated apparatus (Biacore 3000) that allows for a precise determination of the IC50.

More particularly, SPR inhibition experiments were performed on a Biacore 3000 instrument at 25° C. Measurements were carried out on 2 channels with 2 immobilised sugars: α-L-fucose (channel 1), α-D-galactose (channel 2). Immobilization of sugars was performed at 25° C. using running buffer (HBS) at 5 µL/min. Immobilization on each channel (CM5 Chip) was performed independently as follows. First, channel was activated by injecting a fresh mixture of EDC/NHS (35 µL, 420 s). Then, a solution of strepatavidin (100 µg/mL in Na acetate pH 5 buffer) was injected (50 µL, 600 s). Remaining reactive species were quenched by injecting ethanolamine (1M, 35 µL, 420 s). Finally a solution of the desired biotinylated-polyacrylamide-sugar (Lectinity, 200 µg/mL) was coated onto the surface (50 µL, 600 s) through streptavidin-biotin interaction. This procedure led to 804 RU (fucoside) and 796 RU (galactoside) of immobilized sugars on channel 1 and 2 respectively. Inhibition experiments were performed with the galactosylated channel 2 and plots represent subtracted data (channel 2-channel 1).

LecA was injected using running buffer consisting of HEPES 10 mM, NaCl 150 mM, $CaCl_2$ 10 mM, Tween P20 0.005%, pH 7.4. Inhibition studies consisted in the injection (150 µL, 10 µL/min, dissociation: 120 s) of incubated (>1 h, r.t.) mixtures of LecA (5 µM) and various concentrations of inhibitor (2-fold cascade dilutions). For each inhibition assay, LecA (5 μM) without inhibitor was injected to observe the full adhesion of the lectin onto the sugar-coated surface (0% inhibition). The CM5 chip was fully regenerated by successive injections of D-Galactose (2×30 μL, 100 mM in running buffer).

Binding was measured as RU over time after blank subtraction, and data were then evaluated using the BIAevaluation Software, version 4.1. For $IC_{50}$ evaluation, the response (Req-fitted) was considered as the amount of lectin bound to the sugar surface at equilibrium in the presence of a defined concentration of inhibitor. Inhibition curves were obtained by plotting the percentage of inhibition against the inhibitor concentration (on a logarithmic scale) by using Origin 7.0 software (OriginLab Corp.) and $IC_{50}$ values were extracted from sigmoidal fit of the inhibition curve.

Method (4)

Isothermal Titration Microcalorimetry (ITC).

The method allows for a direct measurement of the affinity between the glycomimetics and the LecA lectin. The dissociation constant is measured.

More particularly, recombinant lyophilized LecA was dissolved in buffer (0.1 M TrisHCl, 6 μM $CaCl_2$, pH 7.5) and degassed (see Supp. Info. for concentration details). Protein concentration was checked by measurement of optical density using a theoretical molar extinction coefficient of 28000. Carbohydrate ligands were dissolved directly into the same buffer, degassed, and placed in the injection syringe. ITC was performed with a VP-ITC MicroCalorimeter from MicroCal Incorporated. PA-IL was placed into the 1.4478-mL sample cell, at 25° C. Titration was performed with 10-μL injections of carbohydrate ligands every 300 s. Data were fitted with MicroCal Origin 7 software, according to standard procedures. Fitted data yielded the stoichiometry (n), the association constant ($K_a$) and the enthalpy of binding (ΔH).

Other thermodynamic parameters (i.e. changes in free energy, ΔG, and entropy, ΔS) were calculated from the equation: $ΔG=ΔH\ TΔS=-RT\ \ln K_a$ where T is the absolute temperature and $R=8.314\ J·mol^{-1}·K^{-1}$. Two or three independent titrations were performed for each ligand tested.

2) Biochemical Results

For all the four methods above mentioned, the lowest the number, the better the efficiency of the glycomimetics.

Method 1

The results obtained by Inhibition of Hemagglutination are given in Table 1 below.

TABLE 1

| Monovalent | | Tetravalent | |
|---|---|---|---|
| 10 000 μM Comp. 5 | | | 500 μM Comp. 19 |
| 2 500 μM Comp. 10 | 250 μM Comp. 21 | 250 μM Comp. 23 | 625 μM Comp. 25 |
| 250 μM Comp. 14 | Hemolysis Comp. 27 | Hemolysis Comp. 29 | Hemolysis Comp. 31 |

The values given in table 1 are inhibiting concentrations of lectin-induced rec cells agglutination. Monocovalent glycoconjugate compound 14 and tetravalent glyconjugate compounds 21 and 23 are the most efficient. Hemolysis of red cells is observed for tetravalent glycoconjugate compounds 27, 29 and 31 indicating a possible toxicity at the concentration used.

Method 2

The results obtained by Enzyme-Linked Lectin Assays are given in the Table 2 below.

TABLE 2

| Monovalent | | Tetravalent | |
|---|---|---|---|
| 250 μM Comp. 5 | | | 7 μM Comp. 19 |
| 300 μM Comp. 10 | 21 μM Comp. 21 | 7 μM Comp. 23 | 14 μM Comp. 25 |
| 46 μM Comp. 14 | 0.8 μM Comp. 27 | 0.9 μM Comp. 29 | 5 μM Comp. 31 |

The values given in table 2 are IC50 values for the inhibition of labelled-LecA binding to a galactosylated polymer in a multi-well plate assay.

Among the monovalent glycoconjuguates, compound 14 is the most efficient inhibitor (as illustrated in FIG. 4). All tetravalent glycoconjugates inhibit the binding of LecA to galactosylated surface at low concentration. The most efficient compounds are 27 and 29 with IC50 in sub micromolar range.

Method 3

The results obtained by Surface Plasmon Resonance are given in Table 3 below (IC50 values).

TABLE 3

| Monovalent | | Tetravalent | |
|---|---|---|---|
| 58.3 μM Comp. 5 | | | 1 μM Comp. 19 |
| 60 μM Comp. 10 | Solubility to be improved Comp. 21 | 1.1 μM Comp. 23 | 1.2 μM Comp. 25 |
| 2.6 μM Comp. 14 | Solubility to be improved Comp. 27 | Solubility to be improved Comp. 29 | Solubility to be improved Comp. 31 |

The values given in Table 3 are the $IC_{50}$ values for the inhibition of label-free LecA binding to a galactosylated chip surface using Plasmon Surface Resonance.

An example of obtained sensorgrams for different concentration of compound 19 is displayed in FIG. 5, together with the corresponding inhibiting curve. Among monovalent glycoconjugate compounds, only 14 give a strong inhibition of binding. For the tetravalent compounds, 19, 23 and 25 are efficient inhibitors with IC50 in the micromolar range. The other tetravalent compounds were difficult to test with this method since it requires concentrated solutions of ligands that were difficult to obtain due to solubility limitation.

Method 4

The results obtained by ITC are given in Table 4 below.

TABLE 4

| Monovalent | | Tetravalent | |
|---|---|---|---|
| 107 μM Comp. 5 | | | 0.094 μM Comp. 19 |
| 180 μM Comp. 10 | Solubility to be improved Comp. 21 | 239 μM Comp. 23 | 202 μM Comp. 25 |
| 5.8 μM Comp. 14 | Solubility to be improved Comp. 27 | Solubility to be improved Comp. 29 | Solubility to be improved Comp. 31 |

The values given in Table 4 are the values of the Dissociation constant for the interaction in solution of LecA and the glycoconjugated callixarenes. A typical measured thermogram obtained for compound 19 is displayed in FIG. 6.

Among monovalent glycoconjugate compounds, only 14 give a strong inhibition of binding. For the tetravalent compounds compound 19 appears as an excellent inhibitor with dissociation constant of 94 nM. Some of the tetravalent compounds were difficult to test with this method since it requires concentrated solutions of ligands that were difficult to obtain due to solubility limitation.

EXAMPLE III

In Vivo Tests

1) Experimental Conditions

Mice were briefly anesthetized with inhaled sevoflurane. For each mouse, 50 l of a bacterial inoculum of $5 \times 10^8$ CFU/ml was instilled into the lungs through a gavage inserted into trachea via the oropharynx. The alveolar capillary barrier permeability was evaluated by measuring residual $^{125}$I-albumin instilled intratracheally as an alveolar protein tracer in the lungs and its leakage and accumulation in the plasma after 6 h after infection. The intratracheal instillate was a mixture of 1 µCi of $^{125}$I-labeled albumin and 5% bovine albumin together with the P. aeruginosa inoculate and different monosaccharides or glycocompounds. The total radioactivity in the instillate was measured. Fifty microliters of instillate was inoculated into the lungs of each anesthetized mouse. Six hours after instillation, mice were anesthetized with pentobarbital given intraperitoneally. The blood was collected by carotid arterial puncture, and a sternotomy was performed to harvest and measure the radioactivity in the lungs, trachea, and stomach. The quantity of 125l-albumin that leaked into the circulation was calculated by multiplying the activity in a blood sample by the volume of blood.

2) Biological Results

Compound 14 has been compared with two monosaccharides: glucose and galactose, in animal models assays. The compounds (glucose, galactose and compound 14) have been co-instillated in mice lungs together with infecting concentration of Pseudomonas aeruginosa. The protection that these compounds bring to the lung was estimated by measuring the integrity of the alveolar barrier. For this, labelled albumin was circulated in the blood and the quantity that leaked through the alveoles barriers to the lung was estimated.

FIG. 7 displays the protective effect of glucose, galactose and compound 14 in a mice model with infection by P. aeruginosa. The permeability measures the deterioration of the alveolar barrier, i.e. the lung tissue damages caused by the bacterial infection.

The monovalent glycoconjugate compound 14 appears to be more efficient than galactose. Its co-instillation results in approximately 50% reduction of lung damages when compared to the control experiment with instillation of bacteria without sugar. The result indicates that compound 14 efficiently protect the lung tissues from destruction by P. aeruginosa and resulting systemic infection.

The invention claimed is:

1. A calixarene-based glycosylated compound (I) having the formula:

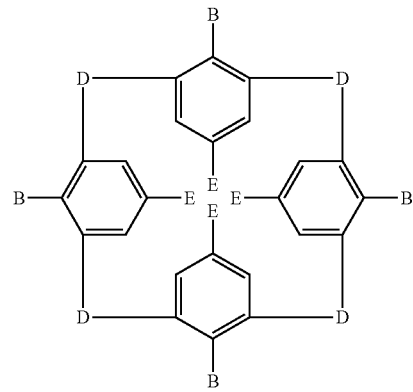

(I)

wherein
D is independently selected in the group comprising a —CH$_2$— group, an oxygen atom, a sulphur atom, a sulfinyl group or a sulfonyl group,
E is independently selected in the group comprising a hydrogen, an alkyl having from 1 to 10 carbon atoms, an aryl having from 6 to 20 carbon atoms, a nitrogen dioxide group, an azide group, an amino group, a guanidinium group, a halogen atom, a —CH$_2$R group wherein R is a hydroxyl, a halogen, an amino group, a N(alkyl)$_2$ group, a NH(alkyl) group, or E represents a —CO—R' wherein R' is a hydrogen atom, a hydroxyl group or an amino,
B represents a A-C group wherein
A is independently selected in the group comprising an oxygen atom, a sulfur atom, a NH group or a (CH$_2$)$_i$ group, i being an integer from 1 to 10,
C is independently selected in the group comprising a hydrogen, an alkyl, an alkenyl, alkynyl,
or C is a group of formula:

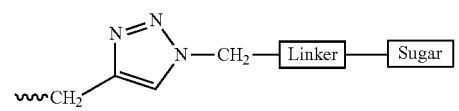

wherein
the linker is a group of formula:

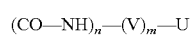

wherein
n is an integer from 1 to 3,
V=CH$_2$, C$_6$H$_4$ (phenyl "Ph"), CH$_2$—CH$_2$-0-CH$_2$, CH$_2$—CO—NH—CH$_2$,
m is an integer from 1 to 15,
U is absent or is CH$_2$,
the sugar is a group having at least one carbohydrate moiety and is selecting in the group comprising:

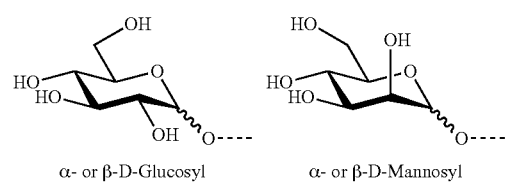

α- or β-D-Glucosyl    α- or β-D-Mannosyl

-continued

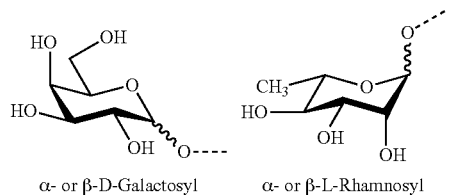

α- or β-D-Galactosyl          α- or β-L-Rhamnosyl

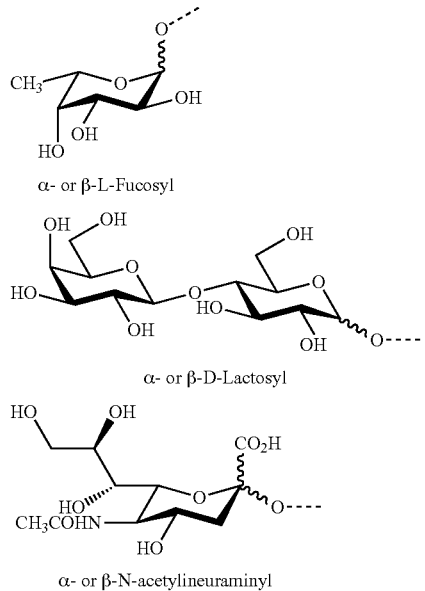

α- or β-L-Fucosyl

α- or β-D-Lactosyl

α- or β-N-acetylineuraminyl or their derivatives,
wherein the sugar derivatives in the C group are selected in the group comprising:

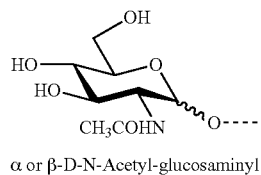

α or β-D-N-Acetyl-glucosaminyl

α or (D-N-Acetyl-glucosaminyl

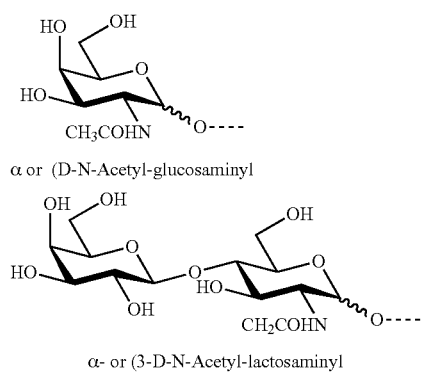

α- or (3-D-N-Acetyl-lactosaminyl

-continued

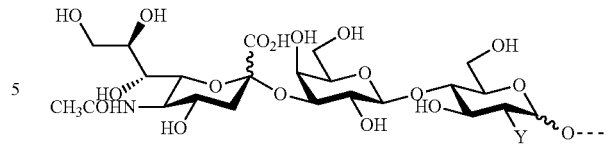

Y = OH
3′-Sialyl-α- or β-D-lactosyl

Y=NHCOCH$_3$

3′-Sialyl-α- or β-D-N-Acetyl-lactosaminyl and

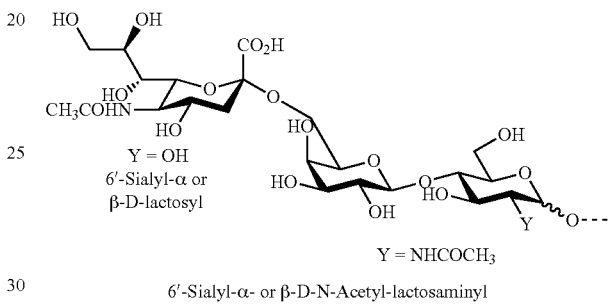

Y = OH
6′-Sialyl-α or β-D-lactosyl

Y = NHCOCH$_3$
6′-Sialyl-α- or β-D-N-Acetyl-lactosaminyl

Or in the group comprising:

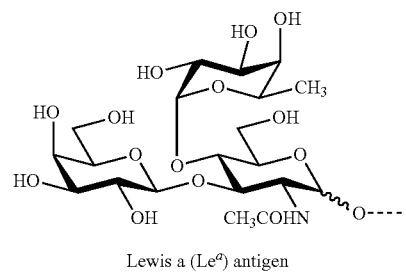

Lewis a (Le$^a$) antigen

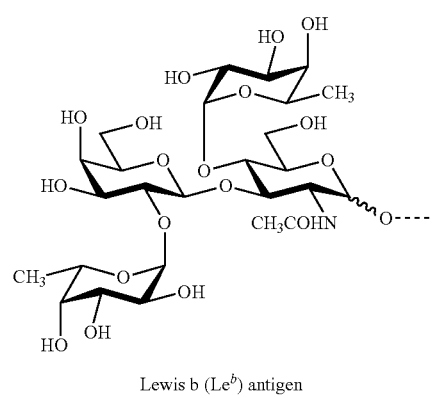

Lewis b (Le$^b$) antigen

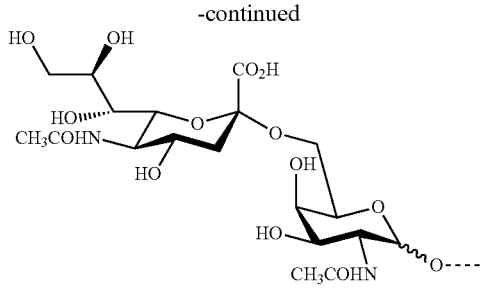

Sialyl Tn (STn) antigen

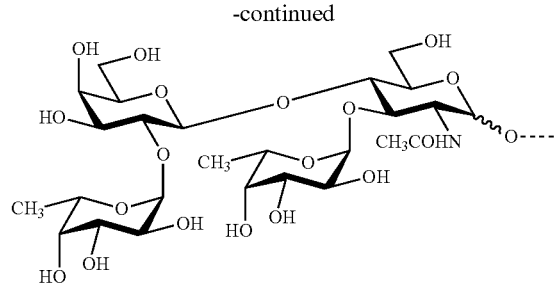

Lewis y (Le^y) antigen

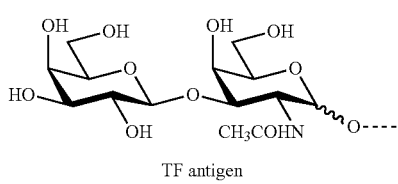

TF antigen

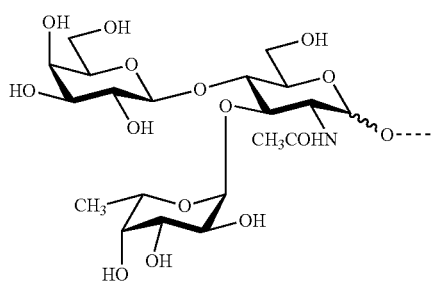

and

Lewis x (Le^x) antigen

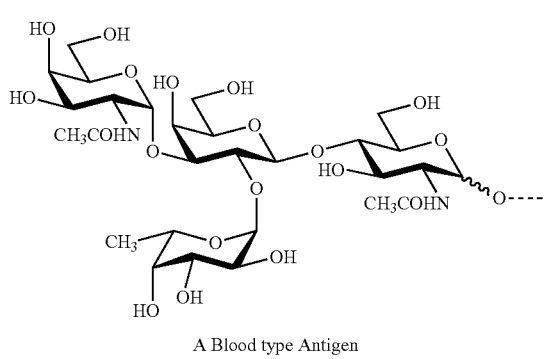

A Blood type Antigen

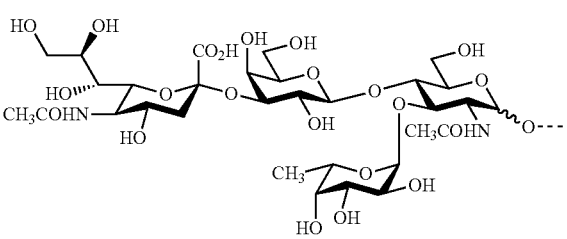

Sialyl Lewis x (sLe^x) antigen

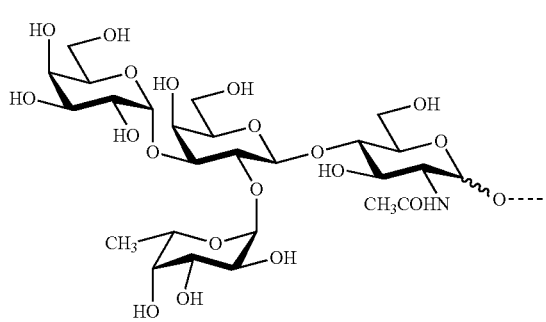

B Blood type Antigen

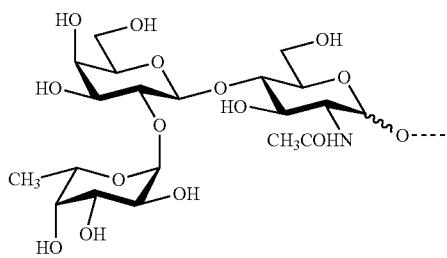

O Blood type Antigen and wherein at least one of the four C groups of the calixarene-based glycosylated compound (I) represents the group of formula:

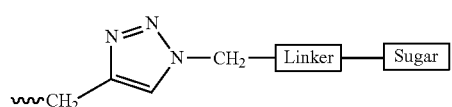

as defined above.

2. A calixarene-based glycosylated compound (I) according to claim 1, wherein the sugar defined in the C group is selected in the group comprising β-D-galactosyl, α-D-mannosyl and α-L-fucosyl.

3. A calixarene-based glycosylated compound (I) according to claim 1, wherein the linker defined in the C group is selected in the group comprising n=1, m=1, V=CH$_2$—CH$_2$-0-CH$_2$, U=CH$_2$, n=1, m=1, V=C$_6$H$_4$ ("Ph"), U=absent, n=1, m=1, V=CH$_2$—CO—NH—CH$_2$, U=CH$_2$.

4. A calixarene-based glycosylated compound (I) according to claim 1, wherein two of the four C groups of the calixarene-based glycosylated compound (I) represent the group of formula:

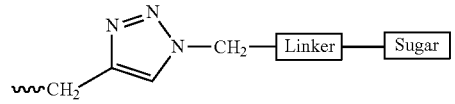

5. A calixarene-based glycosylated compound (I) according to claim 1, wherein three of the four C groups of the calixarene-based glycosylated compound (I) represent the group of formula:

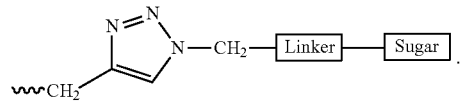

6. A calixarene-based glycosylated compound (I) according to claim 1, wherein the four C groups of the calixarene-based glycosylated compound (I) represent the group of formula:

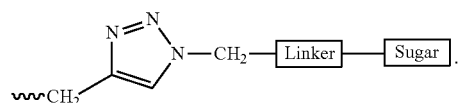

7. A calixarene-based glycosylated compound (I) according to claim 1, wherein D represents a —CH$_2$— group, E represents an alkyl group which is the tert-butyl group and A defined in the B group of the calixarene-based glycosylated compound (I) represents an oxygen atom.

8. A process for the preparation of a calixarene-based glycosylated compound (I) according to claim 1, characterized in that it comprises the following steps:

(a) Preparation of a propargylated calix[4]arene of formula (IV):

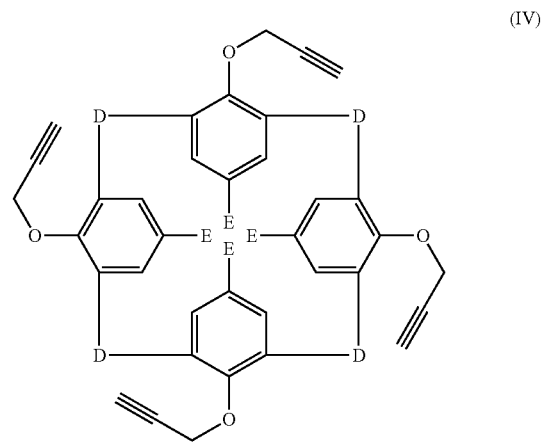

wherein D and E are as defined in claim 1, by regioselective multi-propargylation of a calix[4]arene of formula (V):

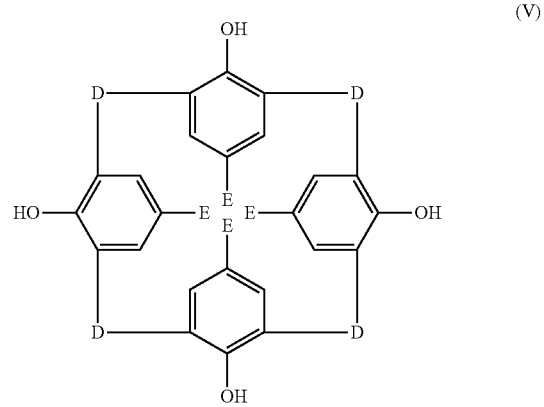

with a propargylated compound of formula (VI):

in the presence of a base to obtain the said propargylated calix[4]arene (IV), (b) Preparation of a protected calixarene-based glycosylated compound of formula (II)

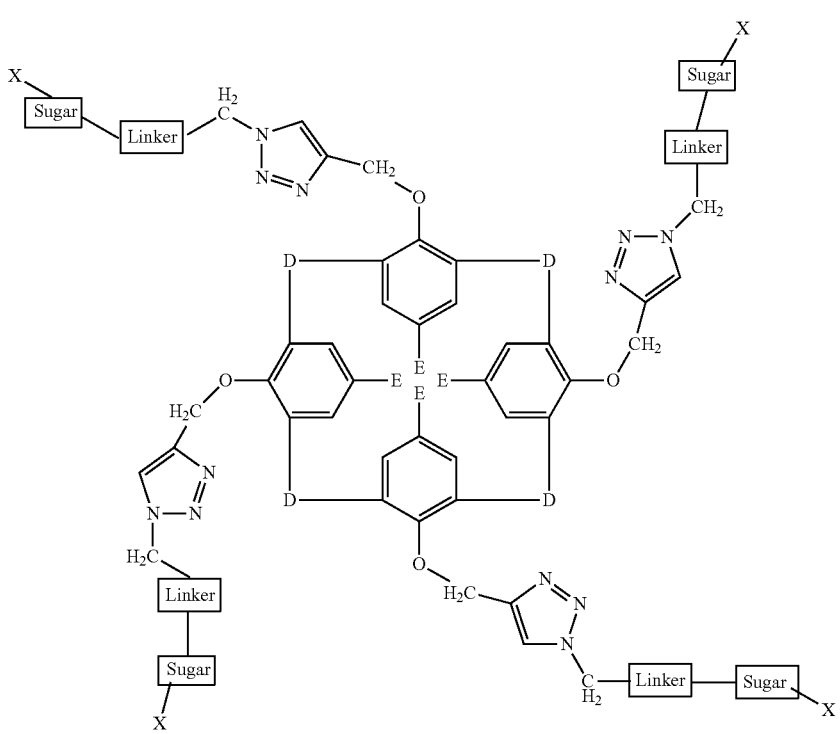

(II)

wherein
the linker and the sugar are as defined in claim 1,
X represents a protecting group selected in the group comprising acetate ($CH_3CO$), benzoate ($C_6H_5CO$) or benzyl ($C_6H_5CH_2$), this protecting group being attached to the oxygen atom of the sugar hydroxyl groups,
by conjugation of the propargylated calix[4]arene (IV) as obtained in the previous step with a carbohydrate derivative of formula (III) bearing an azido functionality next to the end of the linker:

$$N_3-CH_2\text{-Linker-Sugar} \qquad (III)$$

the said carbohydrate being prepared by glycosylation with a linker bearing an alcohol function at one end and an azido group at the other end (c) Obtention of the calixarene-based glycosylated compound (I) as defined in claim 1, by deprotection of the protecting groups of the said protected calixarene-based glycosylated compound of formula (II).

9. A pharmaceutical composition characterized in that it comprises a calixarene-based glycosylated compound (I) according to claim 1, in combination with pharmaceutically acceptable carriers or diluents.

10. The composition according to claim 9, characterized in that it further comprises a therapeutic agent useful as anti-infectious against pathogens that use lectins in the first steps of infection.

* * * * *